United States Patent [19]

MacDonald et al.

[11] Patent Number: 5,840,297
[45] Date of Patent: Nov. 24, 1998

[54] VACCINE COMPRISING ANTI-IDIOTYPIC ANTIBODY TO CHLAMYDIA GLXA AND PROCESS

[75] Inventors: Alex Bruce MacDonald, Amherst, Mass.; Ling-Ling An, La Jolla, Calif.; Elizabeth Sutton-Stuart, Amherst, Mass.; Judith A. Whittum-Hudson, Elkton, Md.

[73] Assignees: Johns Hopkins University; University of Massachusetts

[21] Appl. No.: 34,572

[22] Filed: Mar. 19, 1993

[51] Int. Cl.$^6$ .......................... A61K 39/395; C12N 5/06; C07K 16/00

[52] U.S. Cl. ..................... 424/131.1; 424/151.1; 424/134.1; 424/263.1; 424/150.1; 435/327; 435/342; 435/340; 530/387.2; 530/388.6; 530/388.4

[58] Field of Search ................... 424/88, 131.1, 424/150.1, 151.1, 134.1, 263.1; 435/7.1, 327, 342, 340; 530/388.4, 388.6, 387.2

[56] References Cited

U.S. PATENT DOCUMENTS

| | | |
|---|---|---|
| 4,731,237 | 3/1988 | Reagan et al. . |
| 4,828,981 | 5/1989 | Maggio . |
| 5,246,831 | 9/1993 | Skaletsky et al. . |

OTHER PUBLICATIONS

Harris et al., Therapeutic antibodies –the coming of age. TIBTECH vol. 11:42–44, Feb. 1993.

Waldmann, T.A., Monoclonal antibodies in diagnosis and therapy, Science vol. 252:1657–1662, 1991.

Blanchard, T.G., AN, L.L., Troidle, K.M., Tirrell, S.M., and MacDonald, A.B. Internal Image of Exolipid Genus Specific Antigen Produced by Anti–Idiotype. in 7th International Symposium on Human Chlamydial Infections, (ED.) W.R. Bowie, Cambridge University Press, pp. 205–208, 1990.

Kennedy, R.C. Dreesman, G.R., Kohler, H. Vaccines Utilizing Internal Image Anti–Idiotypic Antibodies that Momic Antigens on Infectious Organisms. Biotechniques vol. 3(5): 404–408, 1985.

Stuart, E.S. and MacDonald, A.B. Purification of Chlamydial Exoglycolpid by Affinity Chromatrography Using Monoclonal Antibodies, FASEB Meeting 1–5, 1988, Abstract 3427.

Rolf, J.M., Gaudin, H.M., Tirrell, S.M., MacDonald, A.B., and Eidels L. Anti–Idiotypid Antibodies that Protect Cells Against the Action of Diptheria Toxin. Proc. Am. Acad. Sci. 1989, vol. 6, pp. 2035–2039.

W.J. Harris and G. Winter Antibody–Based Therapy–Humanized Antibodies Tips May 1993 G. Winter.

A.B. MacDonald et al. A Possible Anti–Idiotypic Vaccine Using Monoclonal Antibody to Chlamydia Group Antigen, Proceedings of the European Society for Chamydia Research, Jun. 1, 1988.

J. L. Marx Making Antibodies Without the Antigens Science vol. 228 pp. 162–165.

Zhou, E–m et al, Microbiology Sciences, 4(2):36–40, Feb. 4, 1987.

Kennedy, RC et al, Scientific American, 255:48–56, 1986.

*Primary Examiner*—Susan A. Loring
*Attorney, Agent, or Firm*—Paul J. Cook

[57] ABSTRACT

A genus specific chlamydia vaccine is provided which comprises an anti-idiotype antibody capable of producing in an animal an anti-anti-idiotypic antibody which recognizes a glycoplipid exoantigen (GLXA) of chlamydia. The vaccine is produced by producing an idiotypic antibody to GLXA which, in turn, is utilized t produce the anti-idiotypic antibody comprising the vaccine.

17 Claims, 9 Drawing Sheets

VACCINE COMPRISING ANTI-IDIOTYPIC ANTIBODY TO CHLAMYDIA GLXA AND PROCESS

BACKGROUND OF THE INVENTION

This invention relates to a vaccine against chlamydial antigens, a process for making the vaccine, and a process for immunizing a human or an animal against chlamydia and a process for assaying for chlamydia infection.

Chlamydial infection is a diverse group of conjunctival, genital, respiratory, and neonatal infections occurring primarily on mucosal surfaces. The etiologic agent of the infection is an obligate intracellular bacterial parasite of eukaryotic cells, chlamydiae. There are three genetically different species in this genus, with certain similarities in morphology, intracellular developmental cycle and antigenic responses: *Chlamydia trachomatis, Chlamydia psittaci* and *Chlamydia pneumoniae*.

The infection by *C.trachomatis* is limited to humans. Fifteen serovars are differentiated based on the antigenic variations of the major outer membrane protein (MOMP) (Grayston and Wang, J. Infect. Dis., 132:87, 1975). Serotypes D–K, is the most common cause of sexually transmitted venereal diseases. Conservatively, more than 4 million cases of chlamydial sexual infections occur each year in the United States making it more prevalent than all other sexually trans-mitted diseases combined. The diseases include nongonococcal urethritis, mucopurulent cervicitis, acute epididymitis, ectopic pregnancy and pelvic inflammatory disease (PID, endometritis, salpingitis, parametritis and/or peritonitis). The infection in women can be quite damaging: Ten percent of the 250,000 cases of pelvic inflammation diseases caused by this organism in the U.S. each year, lead to infertility. When infants born to chlamydia-infected mothers, they are at high risk of developing inclusion conjunctivitis and pneumonia. *C. trachomatis* serovars A, B, Ba, and C cause trachoma, an infection of conjunctival epithelial cells. The chronic and secondary infections induce the infiltration of subepithelial lymphocytes, forming follicles and the invasion of fibroblasts and blood vessels to the cornea, leading to blindness. On the other hand, the formation of the scar and malformation of the eyelid, causes constant scraping of the cornea by the eyelash which can also lead to corneal opacification and blindness. There are approximately 500 million trachoma cases in the world, and between 7 and 9 million are now blind because of its complications making it the world's leading cause of preventable blindness. The prevalence of active trachoma is high in early age. There are 80 million children in need of treatment. It has been an enormously important health problem in the Middle East, North Africa, South Asia and North India.

*C. psittaci* mainly affects animals and birds. It had, and still has a great economic impact in dairy, wool and meat industries. There are 9 serovars from mammalian species, 7 serovars from avian species and 2 biovars from koala bears. Mammalian serovar 1, 2, 3, and 9 infect cattle and sheep, causing a wide range of disorders from placenta and fetus infection and other reproductive problems, including polyarthritis-polysisitis, encephalomyelitis, conjunctivitis as well as intestinal infections. Although numerous attempts have been made to produce vaccines, only modest success has been achieved (Schnorr, J. Am. Vet. Med. Assoc. 195:1548, 1989). Serovars 4, 5, and 6 are the causes of abortions, pneumonia and polyarthritis in porcine species. Serovar 7 represents chlamydial strains of feline conjunctivitis, rhinitis and pneumonitis and serovar 8 includes guinea pig inclusion conjunctivitis. The avian strains often cause human infection in bird handlers and poultry processing workers.

*C. pneumoniae* is a newly identified species. To date, one serovar has been identified, TWAR (Grayston, Proceedings of the Seventh International Symposium on Human Chlamydial Infections, Pg. 89, 1990). Current evidence suggests that *C. pneumoniae* is a primary human pathogen that is transmitted from human to human and causes about 10–20% of community acquired pneumonia in adults. It has become the main causative agent of human respiratory diseases such as pneumonia, bronchitis, pharyngitis, and sinusitis and a possible agent in reactive arthritis. Epidemics have occurred in hospitals, in the military and families. The serological finding from many countries have shown that 50–55% of adults with antibody against TWAR antigen are specific for *C. pnueunoniae*. It is the major bacterial cause of illness in newborn. The infection to elderly persons and those with chronic diseases may cause serious illness or even death.

The pathogenicity of chlamydial infection is not well understood. It is long known that different individuals infected by these serovars exhibit different clinical manifestations. It has been proposed that it was likely due to the variation of the host immune response. It has been shown that immunologic response to the synthetic Th/B cell epitopes in the various inbred strains of mice is different, indicating that the T helper epitope is recognized in the context of the multiple major histocompatibility complex.

The target of chlamydial invasion are typically epithelial cells of a host. It is still not certain how the chlamydial elementary bodies (EB), (a sporelike, spherical particle, about 300 nm in diameter), enter the host cell: receptor-mediated endocytosis, and/or non-specific high affinity absorption. It has been reported that two proteins, 18 and 32 kD of *C. trachomatis* bind to Hela 299 cell membrane preparations. Recently, another heat-labile membrane protein, 38 kD, was proposed as binding to Hela cell line, suggesting a ligand like mechanism. It has also been proposed that since chlamydia have the ability to infect a wide variety of mammalian cells in vitro, there must be some adherence mechanism for the establishment of the infection. The major outer membrane protein was proposed as such an adhesin. Recently, it has been demonstrated that a heparin sulfate-like glycosaminoglycans present on the surface of chlamydia organisms is required for attachment to host cells. The receptors on the host cells have also been studied. It was suggested that proteins 18,000 and 31,000 kD from Hela cells are the receptors due to trypsin sensitivity for the EB specific binding. It also has been shown that *C. trachomatis* and *C. pneumoniae* bind specifically to a lipid on Hela cells. Nuclear magnetic resonance spectroscopy analysis and atom bombardment mass spectrometry show that it was phosphatidylethanolamine (PE). At the same time ganglio-series glycolipids were found specifically bound to EBs. All those findings suggest that the mechanism of endocytosis by epithelial host cells is still a matter of uncertainty. Once the EBs enter the host cells by endocytosis, depending upon conditions, they are transformed into a metabolically active, non-infectious reticulate body (RB). The prime purpose of RBs is intracellular replication by binary fission using host metabolites. This occurs in a membrane-bounded vesicle, termed an inclusion. This inclusion (endosome) can resist the fusion with the lysosomes of host cells. Each RB eventually gives rise to one or more EBs which can initiate another infectious cycle. Host cells may be lysed by release of inclusion bodies or undamaged by exclusion body exocytons. Surface antigens are thought to direct both phagocytosis and evasion of phagolysosomal fusion.

The treatment of chlamydial infections has relied on the administration of antibiotics. This has been proved effective in the early stages of the infection depending upon proper timing for diagnosis and screening. The problem is that the infection can be asymptomatic. Most patients don't realize its presence until it has occurred for a period of time. In the chronic stage as in the case of genital infection, it has been demonstrated that little can be done to prevent the damage of the reproductive tracts in a monkey infection model.

Vaccines employing the whole organism or sub-units of the organism have been used in an attempt to prevent chlamydia infections caused by members of the trachoma biovars. These attempts, however, have been disappointing, partially due to host hypersensitivity in reaction to the vaccines (Grayston et al, Clini. Med. J. (Republic of China) 8:312, 1961, Wang et al, 1967, Am. J. Opthalmol. 63:1615, Schachter, Pathol. Immunopathol. Res. 8:206, 1989). The patholgenises associated with infections is believed to be a process of delayed hypersensitivity. It is thought that chronic inflammation resulting from repeated reinfection of humans has an important role in the conjunctival infiltration, blinding sequelae of trachoma and scarring of the fallopian tubes which result in infertility and ectopic pregnancy. The surface antigens of elementary bodies have been the focus of research attempting to identify a protective antigen.

Surface components of chlamydia actively interact with host cells and with the host's immune system. They are believed to account for the attachment, endocytosis and the immune response, but the exact nature and regulation of these interactions has not yet been fully identified. Several distinct antigenic components of C. trachomatis, C. psittaci and C. pneumonia have been investigated including the identification, characterization and function in chlamydial infection. Moreover, it is of importance to determine the mechanism of infection and determine the protective antigens. Surface exposed antigens are the main targets of much research since they are accessible to the immune or other defense systems. The antigens most actively investigated include major outer membrane proteins (MOMP) chlamydial lipopolysaccharide, 60-kD heat shock protein (HSPO 60) adhesins and a glycolipid exoantigen termed the exoantigen (GLXA).

In the outer membrane of chlamydia there are three cysteine-rich proteins 57, 40, and 12.5 kD which resembles the matrix proteins of gram-negative bacteria. The 57 and 12.5 kD proteins can not be found in the replicating form of the bacteria RBs. As the major outer membrane protein (MOMP), 40 kD, is abundant in both infectious EBs and RBs. In RBs, the protein could function as pore-forming proteins that permit exchange of nutrients for the reticulate bodies. Genetic and molecular characterization have shown that this protein is composed of four variable segments (VS) interspersed among five constant segments. Those variable segments are surface exposed and have the determinants of serovar, subspecies and species specificity.

The studies on immune responses to this protein are mostly carried out by immunization of animals with purified protein. In vitro neutralization experiments have been conducted using the mixture of poly or monoclonal antibodies specific to MOMP and EBs to infect cell culture. These experiments indicate that the antibodies specific to MOMP protein or one single epitope prevent the inclusion bodies formation in cell culture. The mechanism of the neutralization does not involve inhibition of the attachment or penetration, but rather interferes with the process after internalization. Using monoclonal antibodies generated by the whole elementary bodies of serovar B, the monoclonal antibodies which recognized the immuno-accessible MOMP epitope in dot blot assays, neutralized the infectivity of organisms of monkey eyes. The protection was serovar-specific. In a later experiment by using Fab fragments of the monoclonal antibody, it has been further demonstrated that monovalent Fab neutralized the infection by preventing the attachment to Syrian hamster kidney (HaK) cells. Confirming that the protection is not due to the aggregation of bivalent IgGs. T cell epitopes of MOMP have also been investigated. T cell proliferation responses were found in splenic T cells obtained from A/J mice immunized with MOMP in the presence of overlapping synthetic peptides which represent primary sequence of serovar A MOMP. The synthetic peptides which produced T cell response correspond to surface-accessible serovar-specific epitopes located in variable domains (VD) VD I and VD IV. By using a similar approach, it was found in BALB/cByJ mice that VDIII fragment is T cell dependent. It also has been shown that by using chimeric T/B cell peptides derived from two epitopes of MOMP, one is a conserved T helper cell epitope and the other is serovar A specific neutralizing epitope. Some mice immunized with this peptide produced high-titered serum-neutralizing antibodies, while others did not. Although MOMP has been a most intensively studied surface antigen and the neutralization antisera has been produced in experimental animals, there are still many unsolved questions regarding the immune response. For example, the neutralization of infection is serovar specific, thus, it is limited as a vaccine candidate The neutralization is still limited to in vitro studies, and there has been no convincing in vivo protection from challenge by immunization with any MOMP or chimeric epitopes known.

It has long been known that a chlamydia genus specific antigen was a glycolipid (Dhir et al, J. Immunol. 109:116–122, 1972). Much later, it was found that lipopolysaccharide (LPS) was in the outer membrane of both EBs and RBs of chlamydia. It has a chemical structure similar to enterobacterial LPS of the Re chemotype (Nurminen et al, Science, 220:1279–1281, 1983). The monoclonal antibodies prepared by immunization with EBs of serovar L2 were specifically against LPS of chlamydia, but not LPS from N. Gonorrhoeae, S. typhimurium, or E. coli. However, antibodies produced by S. typhimurium Re LPS or lipid A recognized chlamydial LPS (Caldwell and Hitchcock, Infect. Immun., 44:306, 1984). This demonstrated that chlamydial LPS has an unique antigenic domain compared to other gram-negative bacteria. Further characterization has shown that a chlamydia-specific domain contained in its saccharide portion, 3-deoxy-D-manno-2-octulosonic acid (KDO) with a sequence of -kDo (2-8)-kDo(2-4)- -kDo(kDo$_3$). The 2.8 linked moiety is the structural characteristic of chlamydial LPS. Studies have also been carried out in the distribution and the relocation of LPS on the outer membrane during the developmental cycle. By immunostaining with a monoclonal antibody it was shown that LPS is loosely bound in the membrane during the developmental cycle, and not shed into media.

Chlamydial LPS was thought to be an ideal antigen for the vaccine candidate because of its abundance on the surface and its being antigenic. LPS was suspected as an important virulent determinant in the early steps of the infection and the antibodies specific to it serve some function in resolving the chlamydial infection. However, little is known concerning the biological function of LPS or the immunological response to it. It appears that the antibodies which are specific to LPS only have been useful in the diagnosis of chlamydial infection and location of LPS, but not effective in resolving an infection.

Other genus-specific chlamydial antigens are 57 to 60 and 75 kD proteins which have been identified as related to the heat shock protein (HSP) family. This was done by comparing the sequence of the operons encoding these proteins to the groE stress response operon of E. coli or B. megaterium. The antigenic identity of 57 kD protein was confirmed by the reaction with anti-HSP-60 antiserum. The 60 kD protein elicited an ocular hypersensitivity response in immuned guinea pigs, which was characterized by a predominantly mononuclear macrophage and lymphocyte cellular infiltration (Watkins, et al, Proc. Natl. Acad. Sci. USA 83:7580, 1986, Morrison et al, S. Exp. Med. 169:663, 1989). This was the first indication that an antigen is responsible for delayed hypersensitivity in chlamydial ocular infection. The precise involvement of this protein in stimulating immunopathogenic responses in human chlamydial diseases has not been determined. There is evidence that shows a certain percentage of sera taken from women with PID, ectopic pregnancy and tubal infertility have high anti-chlamydial antibodies reacting to chlamydial HSPO-60 heat-shock protein. However, not every patient serum which has high titer to chlamydia reacts with it, indicating that either HSP-60 is not surface exposed or antigenicity is MHC restricted.

The 75-kD protein was found preferentially transcribed during heat stress of chlamydial organisms. The monospecific antibodies from rabbits raised against 75-kD protein were found to bind to the organism and neutralized the infection in vitro. It is an exposed antigen in the outer membrane.

Genus-specific glycolipid exoantigen (GLXA) was originally isolated from the supernatants of chlamydia infected cell cultures (Stuart and MacDonald, Current Micobiology, 11:123, 1982). It has been characterized chemically, biologically and serologically in recent years.(Stuart and MacDonald, Proceedings of the Sixth International Symposium on Human Chlamydia Infections, p167, 1986, Stuart et al, Immunology, 67:527, 1987). Mass spectrographic analysis indicated that GLXA contains polysaccharides: gulose, (not glucose), mannose and possibly galactose, while the lipid component has fatty acids of chain length C17 and C18:1. There is no KDO or lipid A found in its structure. It is produced and released from the infected cells during the growth cycle in vitro. Transmission electron microscopy utilizing colloidal gold-conjugated goat anti-mouse second antibody to detect the specifically bound monoclonal antibody revealed that GLXA is mostly extracellular 48 hours after the infection (Stuart et al, Immunolgy, 74:747, 1991) which is different from that found for chlamydial LPS. Human sera from patients with clinically defined lymphogranuloma venereum (LGV) contain IgG antibodies which recognize GLXA (Stuart and MacDonald, Immunology, 68:469, 1989), demonstrating the immunoaccessibility in the natural infection. But, there was little information on its function in the chlamydial infection and the immune response to it. The overall immunological reaction to chlamydial antigens is not well understood. It is still not known how the chlamydia evade the host immune surveillance. Antibodies found specific to chlamydial antigens in infected human patients have shown little protection for later infection. Although chlamydia mainly affects mucosal surfaces, the clinical relevance of the IgA immunity to it has not been completely described. The feasibility of chlamydia vaccine depends on producing a protective host defense which may include S-IgGA response, a cell mediated response and possibly a humoral antibody. In addition, the ability to produce large quantities of this antigen indicates a synthetic and/or chimeric antigen may be the method of choice.

Idiotypes have been intensively studied following Jerne's network theory in 1974. One of his major proposals is the self-regulation of the immune system through a network of idiotype-anti-idiotype interactions (Jerne, 1974). It is suggested that the idiotopes on a single antibody molecule can mimic (that is, be the "internal image") of any foreign or self epitope at the molecular level.

All idiotypes of a single immunoglobulin molecule have been found to be located on Fv (fragment variable) region by studies showing that the inhibition of binding of antiidiotytpic antibodies to the idiotype is the same between Fv and Fab(Givol, 1991). In general, anti-idotypic antibodies are divided into three types $Ab_2\alpha$, $Ab_2\beta$ and $Ab_2\epsilon$. Only $Ab_2\beta$ binds to the complementarity determining region, thus only it can be the internal image of the antigen. The occurrence of $Ab_2$ displaying internal image or properties must adhere to the following criteria; (1) binding onto $Ab_1$ and to any other anti-nominal antigen antibodies from another species and lack of reactivity with $Ab_2$ to other antibodies; (2) inhibition of the binding of $Ab_1$ to the specific antigen, the nominal antigen, and (3) the ability to elicit the synthesis of $Ab_3$ with anti-antigen specificity in animals without previous exposure to the antigen (Ertl and Bona, 1988).

The important role of anti-idiotypic antibodies in vivo has been shown in numerous experiments. The administration of anti-idiotypic antibodies was found to elicit different effects: either suppression or enhancement of the responses to the specific idiotype(Hart, 1972, Kennedy, 1983). In autoimmunity, it certainly plays an important role. The pathology associated with many autoimmune diseases is most likely due to (at least in part), a direct idiotype-antiidiotype interaction of the autoimmune antibodies with anti-idiotypic antibodies. Idiotypic specificity in a specific antibody were first characterized, by demonstrating that specific hapten binding could inhibit idiotype recognition. The first experimental support for the validity of the internal image was presented by Sege and Peterson in 1978 by using anti-idiotype as a probe to identify cell surface receptors.

The best information for the exact molecular basis for the mimicking presently is obtained from the X-ray crystallography of the idiotype-anti-idiotype complex. The basis of molecular mimicry of the antibodies can be either local sequence homology to the original protein as in a reovirus system or, in most cases, identical conformations from entirely different amino acid sequences as in the hemoglobin-myoglobin family of proteins. X-ray crystallography and sequence data in the later studies showed that identical, functional conformations can be assumed by proteins that differ by as many as 137 of 141 amino acids. The studies of the crystal structure of idiotope-anti-idiotope complex in the anti-lysozyme antibody and the anti-idiotope have demonstrated that a private idiotope consists of 13 amino-acid residues, most from the complementaritydetermining regions, but including three residues from the third framework region of its VL domain. Seven of these residues are common with the paratope of anti-lysozyme antibody, indicating a significant overlap between idiotope and antigen-combining site. Idiotype has been a unique tool in characterization and manipulation of the immune response since it was found and realized: as a clonal marker to follow B cell development, somatic mutation and fate of clones of B cells. They have been used as a phenotypic marker for germ-line V genes. Anti-idiotypic antibodies which bear the internal image of external pathogens such as virus, bacteria or parasites have been used as surrogate antigens for vaccine and are being used in treating B cell lymphoma and autoimmune disease such as encelphalomyelitis.

Prior to the present invention, production of neutralizing antibodies by using anti-anti-idiotypic idiotype antibody to mimic carbohydrate antigen has been achieved using a bacterial system, Schriver et al, J. of Immunol; 144:1023, 1990.

Accordingly, it would be desirable to provide a means for preparing a genus specific vaccine capable of providing immunization from chlamydial infection. It would also be desirable to provide a means for producing such a vaccine in quantity and to provide a process for increasing the effectiveness of the vaccine.

DESCRIPTION OF SPECIFIC EMBODIMENTS

Figure 1:
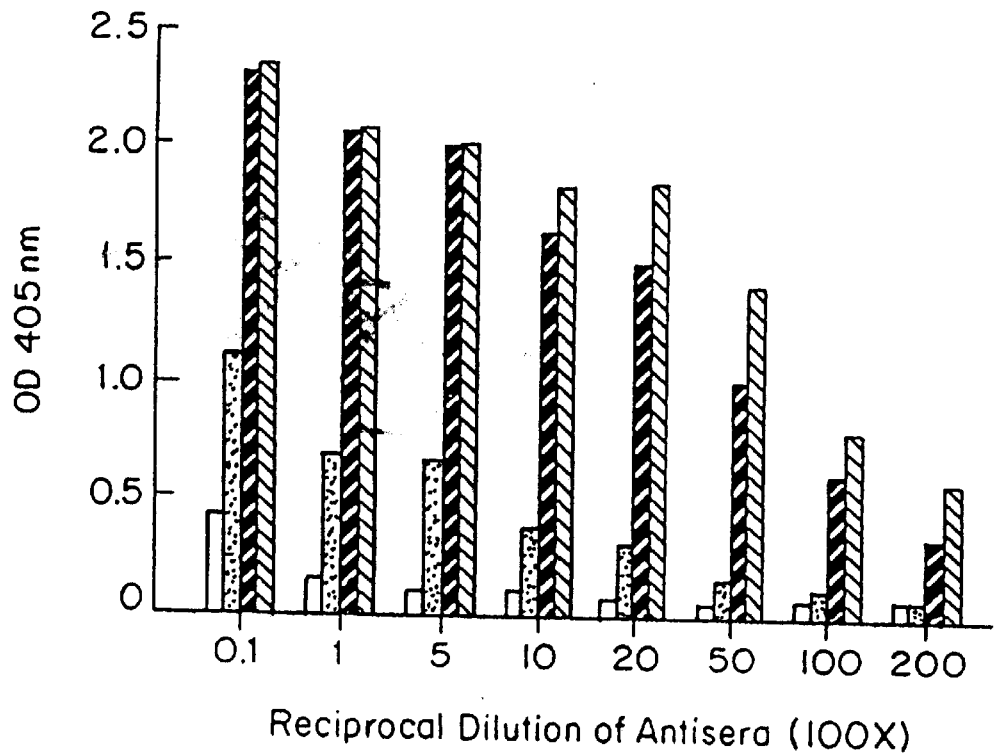
FIG. 1 is a binding curve of guinea pig antisera to monoclonal GLXA-$Ab_1$.
Figure 2:
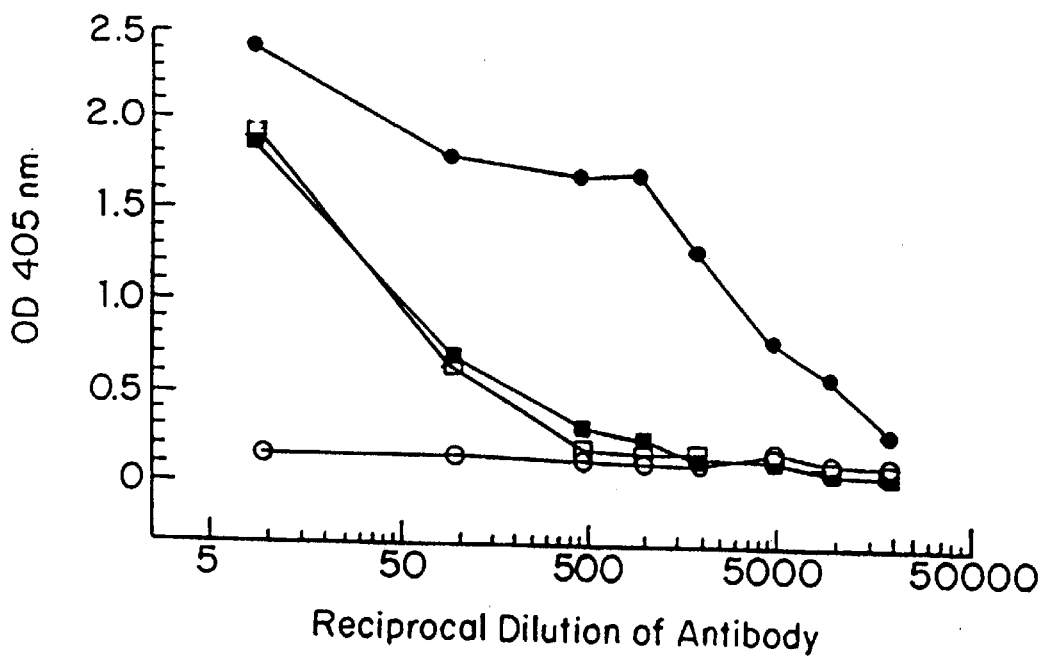
FIG. 2 is a binding curve of guinea pig anti-monoclonal GLXA-$Ab_1$ IgG antisera to normal mouse IgG before and after immunosorption.
Figure 3:
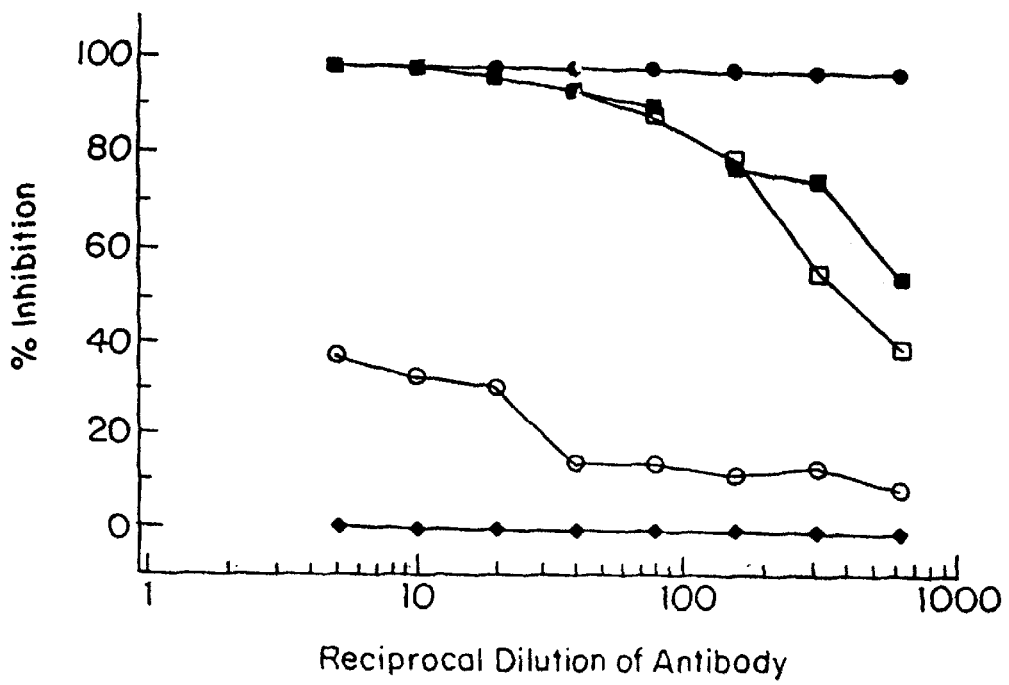
FIG. 3 is a curve showing the inhibition of the binding of monoclonal GLXA-$Ab_1$ to GLXA by absorbed guinea pig anti-idiotypic antisera.
Figure 4:
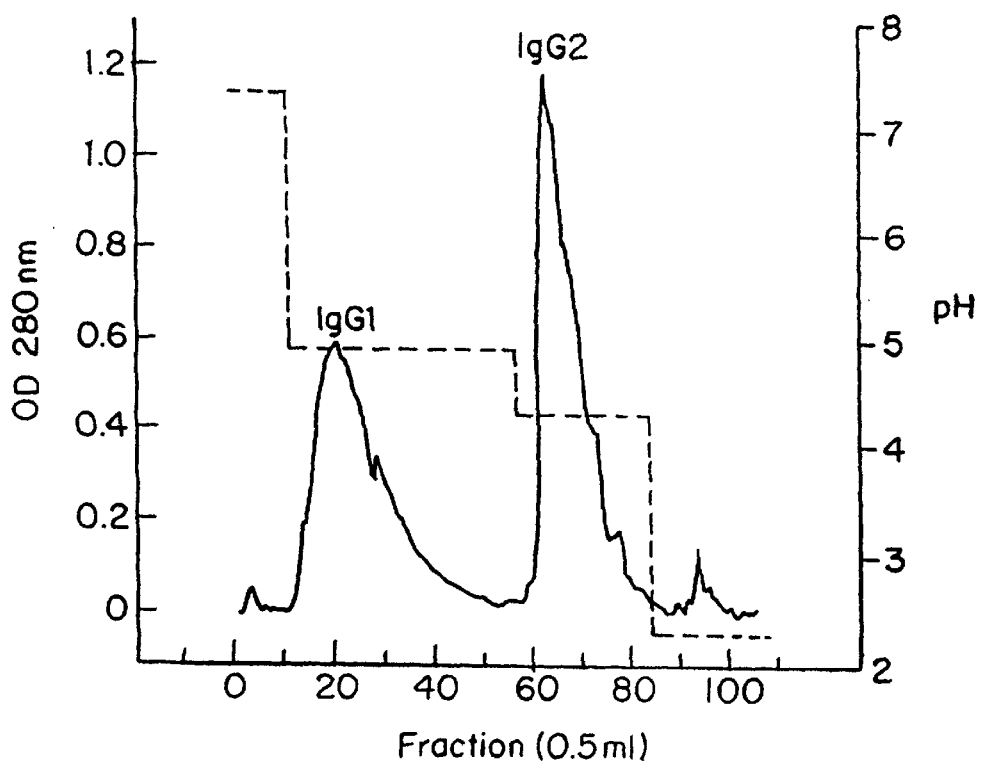
FIG. 4 is a curve showing fractionation of guinea pig anti-idiotypic IgG.
Figure 5:
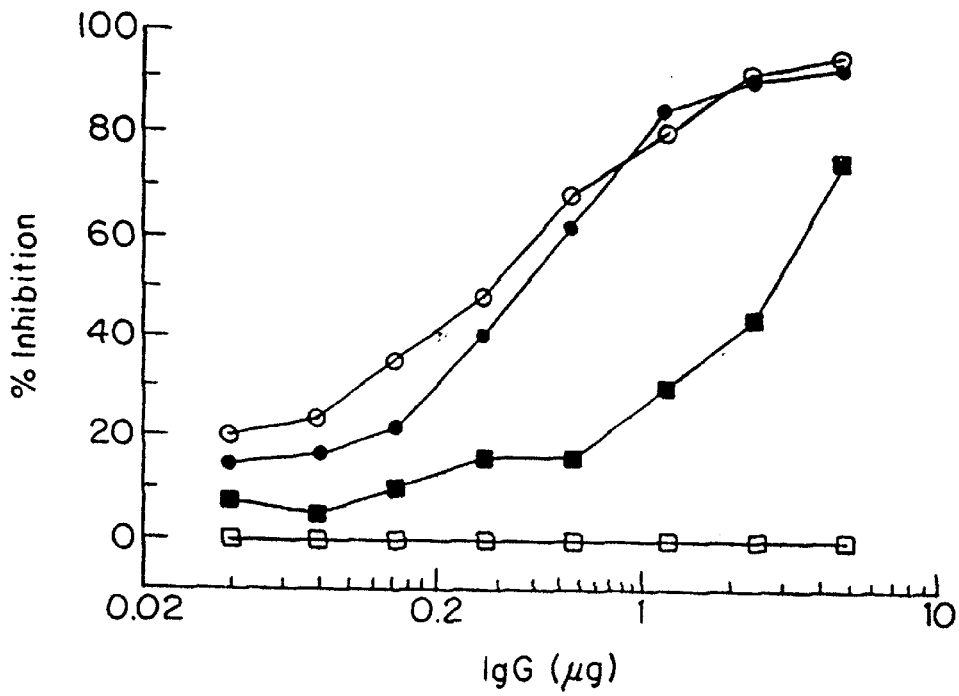
FIG. 5 is a curve showing the inhibition of the binding of monoclonal GLXA-$AB_1$ to GLXA by guinea pig anti-idiotypic isotypes.

The present invention is based upon the discovery that an anti-idiotypic antibody (hereinafter GLXA-$Ab_2$)is capable of producing in an animal an anti-anti-idiotypic (hereinafter GLXA-$Ab_3$) antibody which recognizes GLXA, which is capable of immunizing an animal against chlamydia and is capable of neutralizing chlamydia infection in an animal. In addition, it has been found in accordance with this invention that the useful anti-idiotypic antibody can be either a polyclonal antibody or a monoclonal antibody. In addition, it has been discovered that these activities of the GLXA-$Ab_2$ surprisingly are obtained despite the fact that its predecessor, the idiotypic antibody (hereinafter GLXA-$Ab_1$) from which $Ab_2$ is obtained does not have any significant activity in either immunizing or neutralizing against chlamydia infection.

By using the GLXA-$Ab_2$ to mimic carbohydrate of the glycolipid antigen, the present invention offers an alternative strategy for the conversion of a thymus-independent antigen into a thymus-dependent immunogen because idiotype vaccines are proteins. The availability of GLXA-$Ab_2$ which mimics the chlamydial antigen, GLXA, in accordance with this invention, is of importance: (1) in the elucidation of the immunological mechanisms associated with the carbohydrate epitope present on GLXA (2) its function in chlamydial infection such as the attachment and phagocytosis of the host cells and (3) it provides an essential tool to identify a GLXA specific receptor of the host cells. It also provides a means for producing a chlamydial vaccine.

Monoclonal GLXA-$Ab_2$ is an immugen (i.e., capable of eliciting an immune response) and binding specifically with the products of that response whether they be antibodies and/or cell surface receptors of B cells or T cells. The rapid response to monoclonal GLXA-$Ab_2$ and the memory demonstrated in the re-challenge experiment discussed below in Example I and FIGS. 16A and 16B indicates that a T cell response has been stimulated. This means that the T helper cell is responding to an antigenic determinant (epitope) which differs from the GLXA epitope and is involved in the stimulation of B cells which produce an antibody receptor for GLXA-$Ab_3$ that binds GLXA. In addition, the T helper cell may be of the type which produces cytokines that have been shown to be involved in protective chlamydia infections. Two of these are gamma-INF (gamma interferon) and TNF (tumor necrosis factor).

In accordance with this invention, there is provided: (1) production of polyclonal and monoclonal anti-idiotypic antibodies selected for the internal image of antigenic epitope on GLXA (2) characterization of the anti-idiotypic antibodies and (3) a vaccine which provides immunization, neutralization and protection of chlamydial infection both in vitro and in vivo and (4) a method for detecting the presence of chlamydia in a biological sample.

In accordance with this invention to produce a vaccine active against chlamydia infection, an antibody to GLXA is produced in a first step by any conventional method.

The GLXA is obtained and purified by any presently available method. Thus GLXA can be isolated on an octyl-sepharose column and eluted with alcohol; isolated on DEAE Sepharose and eluted in low pH aqueous solution or isolated on a polyacrylamide bead column and eluted with low pH aqueous solution of KSCN (5M). In a preferred method GLXA is obtained and purified from supernatant of infected cell cultures by presently available methods such as by exclusion chromatography over a Sepharose 6B-Cl column in 0.075M phosphate, 0.154M NaCl, pH 7.2. The GLXA appears in the front fraction of the column and is detected by a chemiluminescense assay using an acridinium ester conjugated monoclonal GLXA-$Ab_1$. The fractions containing the GLXA are usually contaminated by nucleic acids, but not protein. The GLXA fractions are pooled, concentrated and treated with RNase and DNAase at pH 8.0 for about 2 hours at 37° C. The mixture is rechromatographed over the same column and is now pure. It can be stored at 4° C. (with or without preservative).

The antibody can be polyclonal or monoclonal. In the production of monoclonal antibody, an idotypic antibody GLXA-$Ab_1$ is provided by immunizing an animal, usually a mouse with GLXA as the antigen. Immune spleen cells of the animal then are identified, isolated and fused with lymphoma or myeloma cells by being contacted with a fusing agent such as polyethylene glycol such as by the procedure of Kohler & Milstein, Nature 256:459, 1975. The fused cells then are incubated in a selective medium such as HAT medium which precludes the growth of unfused malignant cells. The hybridoma cells are cloned by limited dilution and supernatants are assayed for secreted monoclonal antibody of desired specificity. A suitable hybridoma for producing GLXA-$Ab_1$ is deposited in the American Type Culture Collection and identified as ATCC H.B.11300. Monoclonal antibodies also can be obtained by ascitic growth of hybridomas in vivo. Alternatively, the lymphocyte cells can be immortalized by exposure to Epstein-Barr virus. The idiotype antibody GLXA, $Ab_1$ is useful in producing GLXA-$Ab_2$ which, surprisingly is active in immunizing against or neutralizing a chlamydia infection. In addition, GLXA-$Ab_2$ is not species specific but is genus specific in that its immunization and neutralization activity is useful in many animal species. The monoclonal GLXA-$Ab_2$ also can be produced by the process utilizing hybridomas set forth above for GLXA-$Ab_1$ but by utilizing GLXA-$Ab_1$ as the antigen. Suitable hybridoma for producing GLXA-$Ab_2$ is deposited in the American Type Culture Collection and identified as ATCC H.B.11301. GLXA-$Ab_2$ also can be produced as a polyclonal antibody and, as a polyclonal antibody it is active for immunization against or neutralization of infection by chlamydia. Polyclonal antibodies are made in any conventional manner wherein a first animal is immunized with GLXA as the antigen and poyclonal GLXA-$Ab_1$ is isolated from the animal's serum. The polyclonal GLXA-$Ab_1$ or monoclonal GLXA-$Ab_1$, then is injected into a second animal of a different species from the first animal and polyclonal GLXA-$Ab_2$ then is recovered from the second animal's serum.

Monoclonal GLXA-$Ab_2$ or polyclonal GLXA-$Ab_2$ are both anti-idiotypic antibodies which mimic an antigen comprising a genus specific chlamydial glycolipid exoantigen (GLXA). Both forms of GLXA-$Ab_2$ are useful as a vaccine for immunizing an animal against genus specific chlamydial infection. In addition, both forms of GLXA-$Ab_2$ are useful by being administered to an animal infected with chlamydia in order to neutralize genus specific chlamydia infection.

Also, in accordance with this invention the Fab fragment vaccines suitable for immunizing against or neutralizing chlamlydial infection can be prepared from the Fab fragments of GLXA-$Ab_2$. The Fab fragments can be prepared from GLXA-$Ab_2$ by any conventional means such as by exposing the GLXA-$Ab_2$ to papain or by exposure to trypsin or chymotrypsin followed by reduction and alkylation.

The vaccine is prepared by mixing monoclonal GLXA-$Ab_2$ IgG or the Fab fragment of monoclonal GLXA-$Ab_2$ in a suitable diluent such as aqueous phosphate buffer or the like to give a final concentration of 1 mg per ml of protein. For each administration to a normal size human, for example, fifty ul (fifty ug) to 100 ul (100 ug) of the solution are diluted to 4500 ul which is mixed with 500 ul of a pharmaceutically acceptable adjuvant such as aluminum hydroxide, or aluminum phosphate or the like, (500 ug), or aluminum phosphate ph 6.0+0.1. The particular dosage will vary from animal to animal, depending, for example, upon the animal's weight.

The polyclonal or monoclonal $Ab_2$ of this invention also are useful in determining whether a biological specimen is infected with chlamydia. The $Ab_2$ is utilized in a labeled form in order to determine whether the $Ab_1$ binds with antigenic determinants of chlamydia in a biological sample. The $Ab_2$ can be labeled with an enzyme, fluoropore, radioisotope, or luminescer and the extent of binding, if any, can be determined by determining the extent of subsequent enzyme reaction, fluorescence, radioactivity or luminescence emission in the biological specimen after being exposed to the labeled $Ab_2$. Any conventional assay procedure can be utilized wherein labeled $Ab_2$ or labeled Fab fragment of $Ab_2$ are exposed to a biological sample to determine extent of binding. For example a biological sample can be immobilized at a solid support such as by methanol or ethanol fixation. The sample then is exposed to the labeled $Ab_2$ or Fab fragment of $Ab_2$. The extent of binding then is determined by monitoring the presence of the label. In addition, the $Ab_2$ can be utilized in an unlabeled form by contacting the $Ab_2$ with the biological sample and determining the concentration of immunocomplexes formed, if any.

In another aspect of this invention, the monoclonal GLXA-$Ab_2$ can be utilized to determine the receptor for chlamydia on the surface of eukyrotic cells such as epithelial cells. Either the whole monoclonal GLXA-$Ab_2$ IgG or the Fab fragment of monoclonal GLXA-$Ab_2$ can be complexed with biotin to form a first immunocomplex which then, in turn is contacted with the cells to effect binding of the complex with the cell receptor for monoclonal GLXA-$Ab_2$. The cells then are incubated with labeled avidin which binds to the biotin of the immunocomplex bound to the cell receptor. The label then is detected on the cell to identify the receptor. The labeled cells can be sorted from unlabeled cells by a conventional cell sorter capable of identifying the label such as a fluorescent label. Once the receptor is determined in this manner, the mechanism of cell endocytosis with respect to chlamydia can be determined. Additional labels that can be utilized include radioisotopes, enzymes and luminscence.

The following examples illustrate the present invention and are not intended to limit the same.

EXAMPLE 1

Throughout out this study, two serovars of *C. trachomatis* were used. Serovar B (Strain Har 36) organisms originally isolated from conjunctival scraping of a child, were grown at 37° C. on McCoy cell monolayer with Eagle's Minimum Essential Medium with Hank's balanced salt solution (HMEM, Whittaker, MD) and stored at −70° C. in the same medium with 10% of dimethyl sulfoxide (Sigma Chemical Co., MO). Serovar C (TW-3) was grown in mass tissue culture in McCoy cells. The elementary bodies were purified by centrifugation through renograffin and resuspended in phosphate-buffered saline and stored at −70° C.

A chlamydia free Hartley strain inbred guinea pigs were originally obtained from Jackson Laboratory (Bar Harbor, Me.), bred and maintained in an animal facility. One year old female were used in this study.

Female New Zealand rabbits free of Pasteurella were obtained from Mill Brock Farm (Hadly, Mass.). The rabbits were about 6–8 pounds when received and used within one week. BALB/cByJ (H-2d) mice were obtained from Jackson Laboratory (Bar Harbor, Me.). Young adult cynomolgus monkeys (*Macacca fasicuiareis*) were obtained from Charles River Primates, Inc. (Port Washington, N.Y.) which were free of clinical ocular diseases. All the primates had been used for a previous ocular infection with *C. trachomatis* serovar C elementary bodies, some primates had been previously immunized with a chlamydial protein. The primates challenged in this study, were free of the disease and were not immune. They were randomized prior to the initiation of the experiment. All procedures were performed under anesthesia.

For the production of polyclonal anti-idiotypic antibodies, each of six guinea pigs was immunized subcutaneously with 150 ug of monoclonal GLXA-$Ab_1$ (89MS30) IgG in 1 ml of $H_2O$ plus 1 ml Maalox Plus suspension (William H. Roger, Inc., PA). Three weeks later the guinea pigs were boosted with 100 ug of monoclonal GLXA-$Ab_1$ in 1 ml of Maalox (aluminum hydroxide, alum) and $H_2O$, and were boosted on a monthly basis.

For the production of anti-anti-idiotypic antibodies, three rabbits were immunized with absorbed anti-idiotypic guinea pig isotype IgGl, 300 ug in 1 ml of alum and 1 ml of $H_2O$ intradermally on multiple sites and boosted three weeks later using the identical protocol. Subsequently, rabbits were boosted at monthly intervals. For the production of monoclonal anti-idiotypic antibody, GLXA-$Ab_2$ (91 MS441), fifty ug of KLH conjugated monoclonal GLXA-$Ab_1$ IgG was injected intraperitoneally into five 9-week old female BALB/cByJ mice in an equal amount of complete Freund's adjuvant (Sigma, MO). The same amount was used in the subsequent booster at day 14 and later on a weekly basis for five weeks in the presence of incomplete Freund adjuvant. A final booster injection was given 3 days before the removal of the spleen. For the protection of chlamydial infection experiment, two groups of BALB/c ByJ mice (6 to 20 in each group) were immunized with 50 ug of monoclonal GLXA-$Ab_2$ IgG or 50 ug of normal mouse IgG per mouse subcutaneously with or without Maalox and boosted on weekly basis for three weeks.

Monoclonal GLXA-$Ab_1$ IgG was isolated by protein A affinity chromatography. The ascites which contains monoclonal GLXA-$Ab_1$ IgG was first passed through glass wool to remove lipid and centrifuged 2000 rpm for 10 minutes to remove precipitates. The affinity column (1.5×9 cm) was packed with 2 ml Protein A Sepharose CL4B (ZYMED, CA) was first equilibrated in a binding buffer (1.5M glycine, 3M NaCL, pH 8.9) (Jackson ImmunoResearch Laboratories, PA). Two ml ascites diluted with equal amount of binding buffer was loaded onto the column at 0.6–0.8 ml/minute. The column was stopped for about 30 minutes to allow binding and then rinsed with about three bed volume of binding buffer. The bound IgG was eluted with 0.1M citric acid, pH 3, into glass tubes which contained 50 ul 1M TBS, pH 8.0 to equilibrate the pH. IgG was detected by an absorption at 280 nm. The absorption larger than 0.1 was pooled and dialyzed against 0.075M PBS, pH 7.2 overnight. The purity of the IgG isolated was confirmed by SDS-PAGE on a PhastSystem (Phamacia, N.J.).

Direct enzyme-linked immunosorbant assay

The specific response of guinea pig immunized with monoclonal $Ab_1$ IgG was detected by direct enzyme-linked immunosorbant assay. A 96 well plate with Immulon 2 removable strips (Dynatech, RI) was coated with 0.4 ug of monoclonal $Ab_1$ IgG per well in coating buffer (0.015M $NaHCO_3$, 0.3M glycine, 0.02% $NaN_3$ with 0.06M polyethylene glycol, PEG), pH 9.6. The plate was stored at 4° C. overnight. Each plate was rinsed three times with 0.05% Tween 20 in 0.075M PBS and blocked with 1% BSA/PBS for 2 hours at room temperature. Again, the plate was rinsed three times. The pre-immune sera or antisera from guinea pigs were serially diluted with 0.075M PBS and 100 ul of each was added to each well in duplicate. The mixture was incubated at room temperature for 1 hour and rinsed. Goat anti-guinea pig IgG (H & L) horseradish peroxidase conjugate (Jackson ImmunoResearch Labs, Inc. PA) 1:1000 was added, incubated for one hour and rinsed. TMB substrate (Kirkegaard and Perry Laboratories, MD) was added after rinsing. The absorbance at 405 nm was determined using a Vmax microwell reader (Molecular Devices Corp., CA). The antisera from rabbits immunized with guinea pig IgGl was assayed in the similar manner. Each plate was coated with guinea pig IgGI and the second antibody was goat anti-rabbits (H and L) horseradish peroxidase conjugate (Jackson Immuno Research Labs. Inc., PA).

Preparation of Affinity Chromatography Column

Normal mouse IgG (Jackson ImmunoResearch Labs Inc., PA) was conjugated to Affi-Gel 10 (Bio-Rad Laboratories, CA) as indicated by the manufacturer. Briefly, 5 ml Affi-Gel 10 slurry was transferred to a glass fritted funnel connected to an aspirator and washed with three bed volumes of isopropyl alcohol followed by three beds of ice cold deionized water. Normal mouse IgG (5 mg/ml), 10 ml was mixed with Affi-Gel 10 in a vial. The coupling was done at 4% C overnight with gentle end-to-end agitation. A column (0.9×5 ml) was packed with the coupled gel and rinsed with 0.075M PBS, pH 7.2. The UV absorbance at 280 nm of the effluent was monitored. The highest absorbance of this portion was used to test for protein content by the Bradford Assay (Bio-Rad Laboratories, CA) to evaluate the conjugation.

Absorption of guinea pig antisera with normal mouse IgG

A pool of one guinea pig antisera 3, 4 and 5 weeks after the immunization was absorbed by affinity chromatography on a normal mouse IgG-agarose column. The column was prepared as above. The antisera, about one void volume, was loaded onto the column and incubated for 30 minutes at 4° C. and eluted with 0.075M PBS, pH 7.2. The antiserum was absorbed a second time with a freshly prepared column.

Separation of isotypes of guinea pig IgG

Five ml of guinea pig antisera which had been absorbed by normal mouse IgG, was loaded onto a protein A conjugated Sepharose column, and rinsed with 0.02M phosphate-citrate buffer, pH 7.3. Guinea pig immunoglobulin subclasses IgGl and IgG2 were eluted separately using a step pH gradient of 4.9 until no protein was detected in the effluent. The column was then eluted with a low pH gradient, 4.3. After dialysis against 0.02M phosphate-citrate buffer, pH 7.3, each isotype was subjected to a second round of subclass separation.

*C. trachomatis* serovar B (Har. 36) elementary bodies were propagated in a McCoy cell monolayer in a 2 liter roller bottle (Corning, PA) in HMEM with added L-glutamine (final concentration 0.5 mM), $NaHCO_3$ (final concentration 0.4 mM) and 10% of fetal bovine sera (FBS). Briefly, the medium was removed from the bottle after confluence of the monolayer. Then, 0.5–3.0 ml of EBs suspension (depending on the density of the organisms) in 40 ml of cycloheximide overlay medium (COM) (Whittacker, MD) with added L-glutamine and FBS was inoculated and the bottle was rolled at 3 rpm at 35° C. Two hours later, 200 ml of COM was added and rolling continued for 48 to 72 hours. The supernatant was obtained after centrifugation to remove organisms.

Purification of glycolipid exoantigen, GLXA

GLXA was purified by two steps from the supernatant. First, the supernatant was passed though an Octyl-Sepharose CL4B column and eluted with 95% ethanol (Stuart and MacDonald, Current Microbiology, 11:123, 1984). The antigen in ethanol (antigen content equivalent to 50 ml heavily infected tissue culture supernatant) was concentrated to approximately 50 ul and resuspended in 0.1M phosphate buffer, pH 7.5. to 1 ml. Second, antigen thus prepared was further purified by affinity chromatography. The affinity column was prepared by conjugating monoclonal GLXA-$Ab_1$ IgG to Affi-Gel 10 (Bio-Rad Laboratories, CA) as instructed by the manufacturer. The sample was centrifuged and loaded on to the affinity column and incubated for 30 minutes at 4° C. The column was rinsed with 0.1M phosphate buffer until the eluant became clear. GLXA was eluted in approximately 5M of potassium thiocyanate (KSCN, Mallinckrodt Inc., KY) for about 15–20 ml and dialyzed against 0.075M PBS overnight.

GLXA used in the immuno-dot blot assay of binding of GLXA and monoclonal GLXA-$Ab_3$ by monoclonal GLXA-$Ab_2$ described below was isolated by a size exclusion method. Sepharose 6BLC column (2×100 cm) was equilibrated with 0.075M PBS. The supernatant from *C. trachomatis* serovar F cell culture was first centrifuged 5000 rpm to remove cell debris and approximately 20 ml was loaded onto the column. The flow rate was 0.5 ml/minute. GLXA in the eluant was detected with Magic Lite Analyzer (Ciba Corning Diagnostic Corp., MA). The protocol is as described below.

Chemluminometric immunoassay (Inhibition Assay)

Inhibition of the binding of monoclonal GLXA-$Ab_1$ IgG to GLXA by guinea pig GLXA-$Ab_2$ or rabbit GLXA-$Ab_3$ (antisera, IgG, IgG isotypes) was detected by chemiluminometric immunoassay with a Magic Lite Analyzer (Ciba Corning Diagnostic Corp., MA). The protocol for the inhibition was as follows: Affinity purified GLXA was diluted 1:5 with reagent A (Ciba Corning), mixed and aliquoted into plastic tubes (200 ul/tube, Sarstedt, N.J.). A neutralizing solution Reagent B (Ciba Corning), 100 ul was added to each tube and mixed well. Serial dilutions of guinea pig GLXA-$Ab_2$ or rabbit GLXA-$Ab_3$ IgG, 50 ul were added to each of the above tubes and incubated at room temperature. One hour after the incubation, 100 ul acridium ester-labeled (AE-labeled) monoclonal GLXA-$Ab_1$ IgG in 1% BSA/PBS (between 220,000 to 240,000 relative light units, RLU) was added into the mixture and incubated for one hour. Then, polyclonal anti-chlamydial antibodies which were covalently bound to paramagnetic particles (500 ul) was added to each tube and incubated for another hour. The bound immune complex (paramagnetic particles-GLXA-AE labeled monoclonal GLXA-$Ab_1$ IgG) is separated from the unbound by subjecting the mixture to a magnetic field. The particles were rinsed 3 times. Bound AE-labeled antibody was measured by the Magic Lite Analyzer and RLU were recorded. The percentage of inhibition of binding was calculated as follows:

$$\%\ \text{Inhibition} = \frac{RLU\ \text{control} - RLU\ \text{test}}{RLU\ \text{control}} \times 100$$

where control represents PBS and test represents either pre-immune or antisera (or IgG) added respectively.

Immuno-dot blot Assay

A Bio-rad dot blot apparatus was used for this assay. Poly-vinylidene fluoride (PVDF) membrane, 0.45 um, Immobilon-NC (Millipore, Mass.) was coated with the affinity-purified GLXA or chlamydial rLPS for 18 hours at 4° C. The membrane was then washed with 0.05% Tween 20 in 0.075M PBS buffer, pH 7.2 and blocked for 2 hours at room temperature with 3% BSA/PBS. After rinsing, serial dilutions of rabbit GLXA-$Ab_3$ IgG (90MS699) (isolated by protein A affinity chromatography, method see above) or monoclonal $Ab_1$ IgG (89MS30) were added (100 ul per well), incubated at room temperature for 2 hours, and washed to remove unbound IgG. The PVDF sheet was removed from the apparatus and blocked with 3% BSA/PBS for two hours with gentle agitation, then probed with 1:1000 dilution of peroxidase conjugated goat anti-rabbit IgG (H and L) or rabbit anti-mouse IgG (H and L) (Jackson ImmunoResearch Labs., PA) for 1 hour at room temperature. Unbounded conjugated antibody was removed by washing in a petri dish for 4 times, 5 minutes with agitation. The binding was detected by 4 CN (4-chloro-1-naphthol) membrane peroxidase substrate system (Kirkegaard & Perry Laboratories Inc., MD). Assays were carried out in duplicate.

Biotinylation of IgG

Monoclonal GLXA-$Ab_1$ or rabbit GLXA-$Ab_3$ IgGs were labeled with biotin. Briefly, the GLXA-IgG was first dialyzed against 0.1M sodium borate, pH 8.8 for 4 hours at 4° C. Then, 200 ug of biotinamidocaproate N-hydroxysuccinimide ester (Sigma Chemical Co., MO) per mg of IgG was added, and incubated at room temperature for 4 hours. Finally, 20 ul of 1M $NH_4Cl$ per 250 ul of ester was used and incubated for 10 minutes at room temperature to stop the reaction. Labeled IgGs were dialyzed against 0.075M PBS for 3 days at 4% C.

Immunofluorescence staining of infected McCoy cells

Confluent McCoy cell monolayers were grown on the cover slips in a 24 well plate (Falcon, N.J.) for 24 hours. The medium was taken out from each well before 200 ul of *C. trachomatis* serovar B elementary bodies (Har 36) or 200 ul of HMEM alone were applied to each well. The inclusions forming units (IFU) was approximately 1000/200 ul. Immediately after the application, 200 ul of cycloheximide overlay medium (COM) with L-glutamine and FBS was added to each well. The mixture was incubated at 37° C. for two hours and the medium was replaced by 1 ml COM per well. The plates were then cultured for 48 hours at 37° C. in a humidified incubator with 5% $CO_2$.

After the incubation, cell coverslips were washed with 0.075M PBS twice, 5 minutes each. The coverslips were then blotted with tissue carefully to remove buffer on the coverslips. Then 400 ul of 50 ug/ml biotin-labeled monoclonal GLXA-$Ab_1$ or 400 ul of 1.20 mg/ml of biotin-labeled GLXA-$Ab_3$ was added to the coverslips and incubated at 37° C. for 1 hour. The coverslips were rinsed twice with PBS (five minutes each rinse). Four hundred ul of fluorescein-streptavidin 1:50 in 1% of BSA/PBS was added and incubated for 1 hour. The unbounded fluorescein-streptavidin was rinsed out as above. Fluorescence was detected by photograph with an Olympus 25, 35 mm camera (ASA 400 TMAX black and white Kodak film) mounted on a Zeiss A.7082 Oberkichen microscope, illuminated with a 12 v/100 z halogen lamp.

Neutratization of Chlamydia by GLXA-$Ab_3$ (90MS699) in vivo Inoculums and specimens The rabbit pre-immune and GLXA-$Ab_3$ IgG, normal mouse and monoclonal GLXA-$Ab_1$ IgG were filter sterilized. The IgGs (0.2 mg/ml) were mixed (1:1) respectively with *C. trachomatis* serovar C (TW-3) elementary bodies (2000 inclusion-forming units/20 ul). The mixtures and non-treated EBs (as a control) were incubated at 37° C. for 45 minutes, with gentle shaking every 15 minutes.

After the incubation, approximately 2 ug IgG plus 1000 IFU in 20 ul was inoculated onto inferior fornix of each eye of eight monkeys, four with GLXA-Ab$_3$ IgG plus EBs, two with pre-immune IgG plus EBs and two with EBs only. At the same time, 100 ul of each type of mixture was used to infect 10 wells of 2-day-old McCoy cell monolayer coverslips in a 48 well tissue culture plate for determination of the infectivity of the inocuium. Culture methods are described below.

Conjunctival swabs were taken by sweeping the interior tarsus and fornix, the lateral fornix, the superior tarsus and fornix, and the medial fornix on the day prior to inoculation, and on days 2, 6, 9, 13, and 20 after the inoculation. The swabs were immediately immersed in 2 ml collection medium and disrupted by vortexing for 2 minutes in the collection medium.

Determination of chlamydial infectivity by cell culture

Conjunctival swabs were first disrupted by vortexing for two minutes in the collection medium to collect EBs from the swabs. Then 200 ul of this collection medium was inoculated onto McCoy cell monolayer coverslips. The cells in a 48 well tissue culture plate were grown for two days, 5 wells for each sample. For an in vitro neutralization experiment, 100 ul of the mixture was inoculated onto the monolayer coverslips of 10 wells for each sample. The inoculated plates were then centrifuged at 1,000×g for 1 hour at room temperature. The plates were incubated at 37° C. for 2 hours and the medium were replaced by 1 ml of 10% FBS in COM (Whittaker, MD). The plates were cultured at 37° C. in a humidified incubator with 5% $CO_2$ for 48 hours. The culture medium was aspirated from each well after the incubation. The monolayer coverslips were washed once with 0.075M PBS, fixed with ethanol for 5 minutes and then rinsed with $H_2O$ twice. The fluorescein-labeled mouse anti-chlamydial monoclonal antibody with Evans blue counterstain (Syva, Co., CA.), 25 ul per well was added and incubated for 30 minutes at 37° C. After the incubation, the wells were rinsed with $H_2O$ twice and a cover slip was mounted to each well with mounting fluid. The inclusion bodies were counted by inverting the plate on a fluorescence microscope.

Direct Fluorescent antibody-stained cytology (DFA)

The conjunctival swab (scraping) from each eye of infected primate was pressed on alcohol-precleaned glass slide. The slides were air dried and fixed with cold acetone for 5 minutes. Slides were then dried and 30 ul of fluorescein-labeled monoclonal antibody reagent with Evans blue conterstain (MicroTrak Chlamydia Direct Reagent, Syva Co. CA) were overlaid. The incubation was carried out in a covered, moist chamber. After 15 minutes, slides were turned on edge to remove excess stain and rinsed with deionized water for 10 seconds. Slides were allowed to completely air dry. A cover slip was placed on each slide with mounting medium (Syva Co., CA) and sealed with fingernail polish. Slides were examined under a fluorescence microscope at 500× and 1250×. The infectious titer was scored on a semi-quantitative scale 0–4+: 0 is negative 0.5 is negative on first passage and positive to any degree of second passage, 1 is for 1 to 9 inclusions per well on first passage and so on.

Clinical examination and scoring

The clinical response of each eye was graded as ten clinical signs (Taylor et al, Invest. Opthalmol. Vis. Sci. 29:847, 1988): the follicular response in the lumbar, limbal, superior tarsal, superior fornix, and inferior fornix portion of the conjunctiva hyperemia or injection of the bulbar, superior tarsal, superior fornix, and inferior fornix conjunctiva and ocular discharge. The clinical response was graded on a scale of 0 to 3 for each of 10 signs of conjunctival inflammation to obtain a total inflammatory score for each monkey. The examiner was unaware of the allocation of the monkeys. The means of the scores were used to describe the response of a group of monkeys.

Analysis of Conjunctival Swabs via RNA-directed Hybridization

Total RNA was prepared from conjunctival swab samples taken from GLXA-Ab$_3$ or normal rabbit IgG treated monkeys on the day before the challenge and on day 2, 6, 9, 12, and 20 after the challenge. The swab samples were first homogenized in phenol at 65% in the buffer containing 50 mM Tris (pH 8.0),150 mM NaCl, 10 mM ethylenediaminetetraacetic acid (EDTA), 1% SDS. RNA was precipitated and redissolved in the same buffer. This preparation of RNA was extracted several times with phenol:chloroform (3:1), resuspended and treated extensively with DNase I. The quality of RNA preparation was monitored by ethidium bromide-UV visualization after separation on formaldehyde-agarose gels.

The probe used was a DNA fragment containing the 16S and 23S ribosomal RNA and flanking sequences which was excised from the chlamydial genomic plasmid clone pL2, 434Scl-IA (Cheema et al, The Amer. J. Med. Sci. 302:261–268, 1991). The DNA fragment was labelled by nick translation using 32PdCTP, 800 Ci/m mole (Amersham Corp., IL). The specific activity for all restriction fragment probes was about 106 cpm/ug DNA. Slots on each blot included 1 ug of monkey or human-derived total RNA, 10 pg pure *C. trachomatis* or C serovar RNA (positive control), 3 ug yeast or rat RNA, buffer alone and 1 ug RNA from swabs of each monkey taken prior to infection (negative control). RNA was fixed to 0.22 um filter (Schleicher and Schuell Corp., NH). The hybridization results were visualized via autoradiography at −70° C. using X-OMAT AR film (Kodak, New York).

Production and Characterization of Monoclonal Anti-idiotypic Antibodies (monoclonal GLXA-Ab$_2$)

Conjugation of keyhole limpet hemocyanin with monoclonal GLXA

Monoclonal Ab$_1$ (89MS30) IgG was isolated from a protein A chromatography column as set forth above. The keyhole limpet hemocyanin conjugation was carried out by using glutaraldehyde. Briefly, 1.5 mg of IgG was mixed with 0.05 mg KLH, (Sigma Chemical Co., MO) (approximately 1 molar of IgG per 50 amino acid of KLH) in equal volume of 0.2% of glutaraldehyde in PBS, incubated at room temperature with gentle stirring. One hour later, 1M glycine was added to make a final concentration of 0.02M and incubated for another hour at room temperature. The conjugate was then dialyzed against PBS overnight.

Anti-monoclonal Ab$_1$ hybridoma production

Four days after the last boost (see immunization), spleen cells were isolated from two mice which had the highest titer. Fusion was made with mouse myeloma cell line Sp2/0-Agl4 according to the techniques initially developed by Kohler and Milstein (Nature, 1975) and modified (Golsby, A Practical Guide to Making Hybridomas In Nucleic Acid & Monoclonal Antibody Probes, Swaminathn & Prokask, Eds. Deller. N.Y. pg. 367, 1989). Feeder cell layers were from spleens of mice 8 weeks old.

Screening of Monoclonal anti-idiotypic antibody, 91MS441 (monoclonal GLXA Ab$_2$)

Anti-idiotypic antisera from immunized mice and supernatants from cloned wells were detected by a sandwich ELISA (Uytdehaag et al, J. Immunol, 134:1225, 1985, Hiroshima et al, J. Immunol. 144:224, 1990). Briefly, polystyrene Immulon II microtiter plates (Dynatech Laboratories Inc., VA) were coated with 100 ul of 1 ug monoclonal $Ab_1$ IgG in 0.1M carbonate buffer, pH 8.9 overnight at 4° C. The unbound IgG was removed and the wells were blocked by 3% BSA/PBS for 1 hour at 37° C. After washing, serial diluted antisera or 100 ul of culture supernatant from wells with hybridoma cells was added. After 1 hour incubation at 37° C. and washing, 1 ug of biotin conjugated monoclonal $Ab_1$ IgG was added to each well and the reactivity was detected by the addition of streptavidin-horseradish peroxidase (Jackson immuno Research Labs.,PA). One hour later, TMB peroxidase substrate (Kirkergaard & Perry Laboratories inc., MD) was added. The absorbance was read at 405 nm in a micropiate reader. As positive and negative controls, immune sera taken before the fusion (1:10 dilution) and medium alone were used.

Inhibition of binding Assay

The inhibition of the binding of monoclonal $GLXA-Ab_1$ to GLXA by mouse antiserum and the supernatant of the clones was determined by immuno-chemiluminometric assay as described above.

Generation of ascites

Ten BALB/cByJ mice, age not strictly required, were injected with pristane (2,6,10,14-tetramethylpentadecane, Sigma Chemical Co., MO), 1 ml per mouse intraperitoneally. Ten days later, the mice were injected with approximately $2 \times 10^6$ monoclonal $GLXA-Ab_2$ (91 MS441) producing hybridoma cells. The ascites was harvested by using a Vacutainer 20 g Blood collection needle (Becton Dickinson, N.J.) about ten days later. The ascites was clarified by centrifugation, 2000 rpm for 10 minutes and stored at $-20°$ C. until use.

Isotyping of anti-idiotypic IgG

The isotyping was carried out by ELISA. The supernatant from clone 91 MS441, (100 ul), was coated in each well and incubated at 4° C. overnight. After rinsing and blocking with 3% BSA/PBS for 2 hours, 100 ul of rabbit antiserum specific to mouse subclass: IgG1, IgG2a, IgG2b, IgG3, IgM, IgA, K chain or chain (Bio-Rad Laboratories, CA) was added to each well in duplicate. The plate was incubated at room temperature for one hour. The rabbit antiserum was detected by horseradish peroxidase conjugated goat anti-rabbit (H&L) and TMB substrate (Kirkergaard & Perry Laboratories Inc. MD.

Purification of monoclonal $GLXA-Ab_2$ IgG

The monoclonal $GLXA-Ab_2$ IgG was purified by affinity chromatography on a protein-G-sepharose column. Protein G-Sepharose 4B (Zymed, CA) 5 ml was packed in a 0.5×9 cm column. The ascites (2 ml) was diluted 1:1 with 0.02M phosphate buffer, pH 7.3 and loaded on the column and washed with the same buffer until no protein was detected. The bound IgG was eluted with 0.1M citric-glycine buffer, pH 2.6. The eluant was collected in 1 ml fraction which contained 50 ul of 1M tris-saline buffer, pH 8.0 to balance the eluant. Fractions having UV absorption above 0.1 were pooled and dialyzed in PBS overnight at 4° C. The purified IgG was identified by SDS-PAGE for confirmation.

Immunoprecipitation of monoclonal $GLXA-Ab_2$ by anti-chlamydial antisera from other species Polyclonal antibodies from a human patient diagnosed with a chlamydial infection and chlamydial EBs injected rabbits were tested for the recognition of monoclonal $GLXA-Ab_2$ by ELISA. The procedure was essentially the same as described above with the following exceptions. Briefly, the ELISA plate was coated with 1 ug of monoclonal $GLXA-Ab_2$ per well in 0.075M PBS without coating buffer overnight at 40° C. The wells were rinsed with 0.05% Tween 20 in 0.075M PBS and blocked with 3% BSA/PBS for 2 hours at room temperature. Serial dilution of the patient's serum (92MS273), control human serum (88MS356), rabbit antisera (88MS188) or control rabbit serum (92MS450) 100 ul was added to each well in duplicate. After 1 hour incubation at room temperature, the wells were washed 3 times and 100 ul of peroxidase conjugated goat anti-human or goat anti-rabbit IgG (Jackson ImmunoResearch Labs, MD) was added. TMB substrate was added after one hour incubation. The plate was read on a Vmax microplate reader (Molecular Devices Corp., CA).

Protection from Chlamydia Infection by Immunization of Monoclonal $GLXA-Ab_2$ in a Mouse Infection Model Immuno-dot blot assay of binding of GLXA and GLXA $Ab_3$ raised by monoclonal $GLXA-Ab_2$ Immuno-dot blot assay was done by the same method as described above. The exception is that a PVDF sheet was coated with purified GLXA (100 ul) per lane in 0.075M PBS. Antisera taken from the mice which were immunized with monoclonal $GLXA-Ab_2$ IgG or normal mouse IgG were serially diluted with 3% BSA/PBS. The second antibody was horseradish peroxidase conjugated rabbit anti-mouse IgG (H and L). The photograph was taken by Kodak TMAX 100. The staining intensity of dot blot was scanned by a densitometer.

Inoculation and specimens

C. trachomatis serovar C (TW-3) elementary bodies 5000/20 ul were inoculated onto each eye of the mice which were immunized with monoclonal $Ab_2$ or normal mouse IgG. On the day before the inoculation and on day 7, 10, 14, 21, 28 and 35 after the inoculation, conjunctiva were swabbed from each eye. The area included the inferior tarsus and fornix, the lateral fornix, the superior tarsus and fornix, and the medial fornix. The conjunctival swabs were immediately immersed in the collection medium and disrupted for two minutes by vortex and kept on ice until culturing.

Identification of Receptor on Host Cells by Monoclonal $GLXA-Ab_2$ IgG FACS analysis of the specific binding of monoclonal $GLXA-Ab_2$ to HECEC cells Human endometrial gland epitheria cells (HECEC) were grown in a 75 $mm^2$ flask at 37° C. with 5% $CO_2$. When confluent, cells were scraped off the flask using a cell scraper (Baxter, IL) and centrifuged 200×g for 5 minutes. The cells were rinsed once with 20% FBS in Hanks buffer (Whittker, MD) and passed through a 19 G syringe needle four times to obtain single cells. Serial dilutions of biotin labeled monoclonal $GLXA-Ab_2$ or biotin labeled normal mouse IgG in Hanks buffer, (100 ul) were added to each vial which contained approximately 1.5×106 HECEC cells and incubated on ice for 30 minutes. Each vial was rinsed twice with 0.02% azide in Hanks buffer. Later, 100 ul of FITC conjugated streptavidin was added and incubated for 30 minutes on ice. After washing twice, the cells were kept in 400 ul of sheath buffer on ice. Cells plus FITC conjugated streptavidin and cells alone were used as background control. Single color flow cytometry was performed immediately by FACS scan (Becton Dickinson).

Detection and Characterization of Polyclonal Anti-idiotypic Antibodies

Generation of anti-idiotypic antibodies against monoclonal $GLXA-Ab_1$ in guinea pigs The immunogen which was used to produce the anti-idiotypic antibodies in guinea pigs was a monoclonal antibody identified as 89MS30 (monoclonal $GLXA-Ab_1$). It was originally produced by immunization of BALB/cByJ mice with chlamydial elementary bodies propagated in embryotic egg. Mice spleenocytes were fused with Sp2/0-Agl4 myeloma cells and the clone was screened. The clone (89MS30) reacted to all 15 serovars of C.trachomatis, C. pneumoniae, and C. psittaci 6BC and mouse meningopneumonitis by EIA, demonstrating recognition of a genus specific antigen. The IgG was isotyped as IgG2b by ELISA using rabbit anti-mouse antiserum (Bio-Rad Laboratories, CA). The monoclonal GLXA-Ab IgG was isolated from the ascites with rec-protein A sepharose 4B conjugate column (ZYMED, CA). Inbred guinea pigs (Hartley 13) were immunized and boosted with monoclonal GLXA-$Ab_1$ IgG, 150 ug each in the presence of Maalox, as an adjuvant. Pre-immune sera and antisera were obtained by heart puncture and centrifugation. Five immunized guinea pigs demonstrated strong immune responses against monoclonal $Ab_1$ IgG by ELISA. It was demonstrated that the anti-monoclonal GLXA-$Ab_1$ IgG titer was more than 1 to 20,000 one week after the first boost. These guinea pig antisera kept increasing two weeks after the boost as shown in FIG. 1. FIG. 1 is a binding curve of guinea pig antisera to $mAb_1$ determined by ELISA-for anti-idiotype. Pre-immune sera (□); antisera 3 weeks (⊠) after the immunization; 1 week (■) and 2 weeks after the boost (□). Each value represents the mean of the duplicated determinations.

Complete absorption of guinea pig antisera with normal mouse IgG

In order to remove guinea pig anti-mouse antibodies that are directed against epitopes other than the idiotopes present on the hypervariable regions of the monoclonal $Ab_1$ IgG molecules, the guinea pig antisera was absorbed with normal mouse IgG. The absorption was carried out by affinity chromatography. The column was made by conjugating normal mouse IgG to Affi-Gel 10. The conjugation was evaluated by detecting the amount of unbound protein at absorbance at 280 nm. The highest optical density from a fraction was 0.23, containing 0.18 mg of protein by the Bradford Assay (Bio-Rad Laboratories, CA). The total mouse IgG used in the conjugation was 50 mg, demonstrating that the conjugation was successful. The guinea pig antisera were loaded onto the column and eluted with 0.075M PBS, pH 7.2. This procedure was repeated using a newly prepared column. The antisera before and after the absorption was tested and compared with pre-immune sera for the reactivity to normal mouse IgG by ELISA. The concentration of each antiserum for the assay was equilibrated. Each well was coated with 1 ug of normal mouse IgG. Serial dilutions of pre-absorbed (●); pre-immuned (■) and absorbed guinea pig antisera (□) were added. PBS was background control (○). Horse radish peroxidase conjugated goat anti-guinea pig IgG (H&L) was used as the second antibody. Each value represents the mean of duplicate determinations. The result showed that sera after the absorption had the same reactivity against normal mouse IgG as pre-immune sera (FIG. 2). The unabsorbed antisera had 5 times more reactivity, indicating that all antibodies specific to epitopes other than idiotypes have been completely removed.

Inhibition of the binding of monoclonal GLXA-$Ab_1$ to GLXA by guinea pig antisera If guinea pig antisera contain the specific anti-idiotypic antibody against monoclonal GLXA-$Ab_1$ IgG molecules, the direct effect is that it would inhibit the binding of antigen, GLXA, to the monoclonal antibody, monoclonal GLXA-$Ab_1$. In other words, the antisera bind to the complementarity-determining region of monoclonal GLXA-$Ab_1$ IgG, thus preventing GLXA from binding to the active site. To test this, competition of binding was performed by chemiluminometric immunoassay. Serial dilutions of guinea pig pre-immune sera, unabsorbed antisera, or absorbed antisera were incubated with GLXA which was isolated by immuno-affinity chromatography. After one hour at room temperature, the mixture were incubated with monoclonal GLXA-$Ab_1$ IgG conjugated with acridium ester for additional hour. Solid phase paramagnetic particies were added and a RLU was determined. The inhibiting percentage is calculated as mentioned above. Guinea pig anti-idiotypic antisera exhaustively absorbed with mouse IgG (■), inhibits the binding of $mAb_1$ to GLXA at approximately the same dilutions as unabsorbed guinea pig antisera (□) by chemiluminometric immunoassay. Pre-immune (○); $mAb_1$ (●); and 1×PBS (♦) were included as controls. Percent inhibition in the binding was calculated as described in the text. As shown in FIG. 3, when the guinea pig antisera was diluted 1:40, 95% of the binding of monoclonal $Ab_1$ to GLXA was inhibited by both unabsorbed and absorbed antisera, compared with 15% for pre-immune serum. In addition, the unabsorbed antisera had nearly identical inhibition as absorbed antisera at equivalent protein concentration, indicating that no anti-idiotypic antibodies were removed by absorption. Therefore, a competitive anti-idiotypic antibody had been generated in guinea pigs.

Profile of subclasses of guinea pig anti-monoclonal GLXA-$Ab_1$ IgGs

Previous experiments had shown that different isotypes of guinea pig anti-idiotype exert different effects on the idiotype production. IgGl isotype enhances the idiotype production, whereas $IgG_2$ isotype inhibits the idotype clone. To test the inhibition of different isotype of guinea pig anti-idiotypic IgG, subclasses of IgG were isolated from absorbed guinea pig anti-idiotypic antisera. A step pH gradient of phosphate-citrate buffer was used. IgG and $IgG_2$ were separated and isolated on a protein A affinity column. The elution profile of the isotypes, $IgG_1$ and $IgG_2$ is shown in FIG. 4. The purification of IgG was accomplished by protein A affinity chromatography. Separation of the guinea pig IgG1 and IgG2 was carried out by a step pH gradient of phosphate-citrate buffer. Each peak was identified by immunoelectrophoresis (IEP) with goat anti-guinea pig IgG to immuno-precipitate bands (Bethyl, TX). The first peak which is composed of IgGl was precipitated by both goat anti-guinea pig IgGl and $IgG_2$, but formed a single band by goat anti-guinea pig antisera. The first peak was then repurified by the same method.

Inhibition of the binding by subclasses of guinea pig IgG

The competition by different subclasses of IgG was carried out again by chemiluminometric immunoassay using guinea pig anti-idiotypic antibodies of either $IgG_1$ or $IgG_2$ isotypes. FIG. 5 shows that 0.4 ug IgGl was able to inhibit the binding of monoclonal GLXA-$Ab_1$ to GLXA by 50%. As shown in FIG. 5, inhibition of the binding of $mAb_1$ to GLXA was inhibited by guinea pig anti-idiotypic isotypes. The binding of $mAb_1$ to GLXA was inhibited by guinea pig anti-idiotypic IgG1 (●) and partially by IgG2 (■) in chemiluminometric immunoassay. Homologous unconjugated $mAb_1$ (○) or PBS (□) were used as controls. Percent inhibition in the binding was calculated as described above. The total inhibition occurred when 100 ug was used. This was essentially the same concentration needed when unlabled monoclonal GLXA-$Ab_1$ IgG was used. $IgG_2$ showed little, if any, inhibition, approximately 25% of the binding of monoclonal GLXA-$Ab_1$ to GLXA with 1.0 ug. These data demonstrate that the $IgG_1$ subclass of anti-idiotypic IgG was at least 5 times more inhibitory than the $IgG_2$ subclass.

Generation of Anti-anti-idiotypic Antibodies (GLXA-Ab$_3$) in Rabbits by Guinea Pig IgG1

Figure 6:
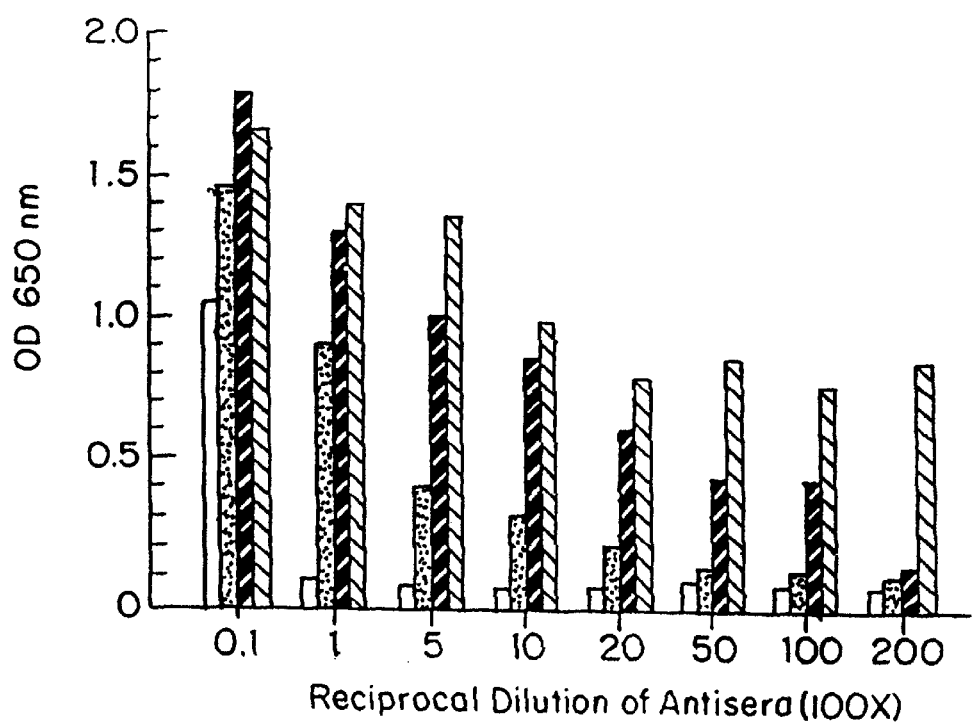
FIG. 6 is a curve showing the binding of rabbit anti-anti-idiotypic antibody to guinea pig anti-idiotypic IgG.

The evidence obtained showed that guinea pig anti-idiotypic IgG1 was against the hypervariable region of monoclonal GLXA-Ab$_1$ IgG and also inhibited its binding to GLXA. The final criteria of an internal image of the anti-idiotypic antibodies is to confirm structurally that the Ab$_2$ is Ab$_2\beta$ not Ab$_2\alpha$ or Ab$_2\epsilon$. Since Ab$_2$ binds to the framework portion of immunoglobulins, it can also inhibit the binding of Ab$_1$ to the cognate antigen. To confirm that guinea pig anti-idiotypic IgG1 is Ab$_2\beta$, the isotype IgG1 was used to produce an anti-anti-idiotypic antibody (GLXA-Ab$_3$) which can recognize the GLXA epitope in an animal which has never been exposed to GLXA antigen, (Ertl et al, Proc. Natl. Acad. Sci. USA 81:2850,1988). Three New Zealand white rabbits were immunized with guinea pig anti-idiotypic IgG1 in the presence of adjuvant, Maalox (alum). The antisera from one rabbit (S2) were tested against IgG1 by ELISA (FIG. 6). The specific reactivity of rabbit antisera to guinea pig IgG1 was determined by ELISA. Guinea pig IgG1 was used as the antigen and goat anti-rabbit IgG HRP conjugate used as the second antibody. Titer shows rabbit anti-anti-idiotypic antisera 3 weeks after the immunization (⊠); 1 week (■) and 3 weeks (after boost. Pre-immune serum was used as a control (□). The titer increased with time after the immunization. The titer was much higher than 20,000 compared with pre-immune sera three weeks after the boost.

Anti-anti-idiotypic antibodies from rabbits recognize GLXA

Figure 7:
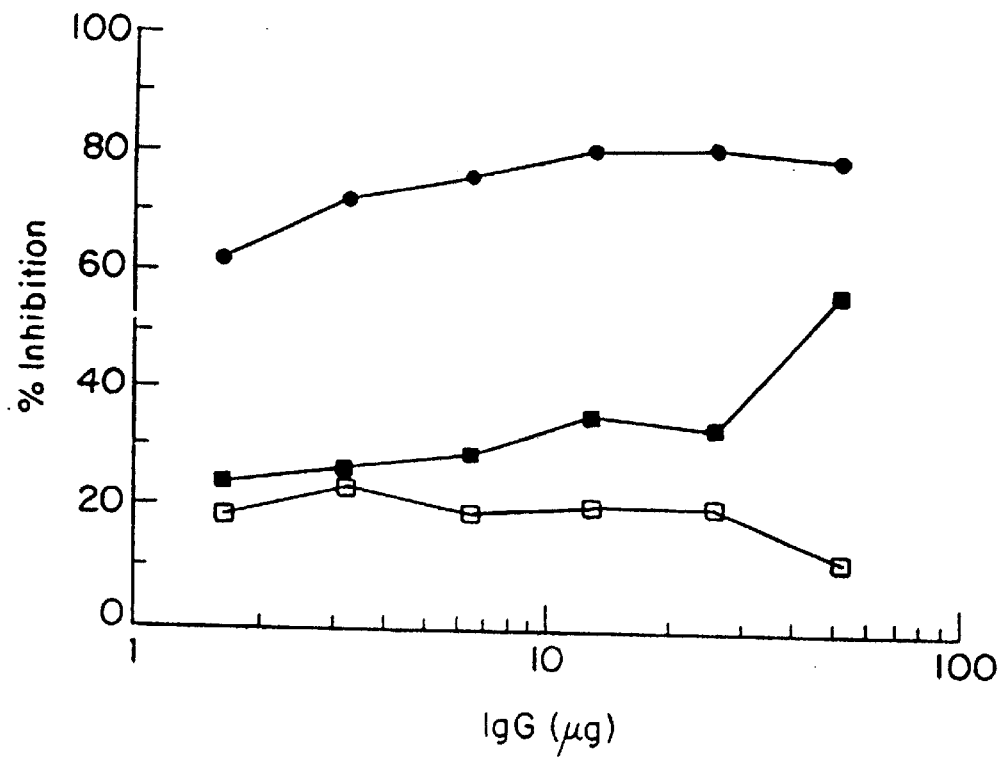
FIG. 7 is a curve showing the binding of monoclonal GLXA-$Ab_1$ to GLXA by rabbit GLXA-$Ab_3$.

The dot blot apparatus (Bio-Rad Laboratories, CA) was used to detect the reactivity of rabbit antisera to GLXA. Antisera from two rabbits were tested by immuno-dot blot assay. Since monoclonal GLXA-Ab$_1$ is cross-reactive to chlamydial LPS, polyvinylidene fluoride (PVDF) membrane was coated with both GLXA and chlamydial rLPS. Both rabbits antisera recognized GLXA and LPS with high reactivity. When IgG from rabbit (S2) (90MS699) was used, the dots were positive at a concentration of 0.006 ug per lane. Pre-immune IgG did not react. The IgG isolated from this antisera was tested for its capacity of inhibiting the binding of monoclonal GLXA-Ab$_1$ to GLXA, since GLXA-Ab$_3$ produced by the internal image, GLXA-Ab$_2$ should exhibit a similar binding. This is confirmed as shown in FIG. 7. Serial dilution of pre-immuned (□) rabbit Ab$_3$ antibody (■) mAb$_1$ (●) IgG are evaluated for the binding in the chemiluminometric immunoassay. The percent inhibition obtained from the means of the duplicatess determinations. The inhibition by GLXA-Ab$_3$ increases with concentration, but about five times less inhibitory compared to unlabeled monoclonal Ab$_1$. This demonstrates that the guinea pig anti-idiotypic antibody IgG1 is the internal image of antigen, GLXA. GLXA-Ab$_3$ IgG was further tested for the recognition of elementary bodies of C. trachomatis in vitro.

Monoclonal GLXA-Ab$_1$ and GLXA-Ab$_3$ IgG were conjugated with biotin by glutaldehyde. Labeled monoclonal GLXA-Ab$_1$ or GLXA-Ab$_3$ was incubated with McCoy cell monolayer on coverslips which were infected with C. trachomatis serovar B (Har 36) elementary bodies for 48 hours. Non-infected monolayers were used as control. The fluorescence staining pattern of the elementary bodies by monoclonal GLXA-Ab$_1$ and polyclonal GLXA-Ab$_3$ IgGs demonstrated that GLXA-Ab$_3$ not only recognized the purified form, but also native form of GLXA.

Neutralization of the Chlamydial Infection in Primates by GLXA-Ab$_3$ IgG (90MS699)

The next question concerned the ability of monoclonal GLXA-Ab$_1$ or GLXA-Ab$_3$ to neutralize chlamydia elementary bodies and thus protect host cells from infection. The experimental approaches utilized to answer this question involved neutralization of infection in cultured cells and neutralization of the infection in primate conjunctiva.

In vivo GLXA-Ab$_3$ neutralizes chlamydial infection whereas monoclonal GLXA-Ab$_1$ does not.

Neutralization in primate conjunctivae was determined by preincubating organisms with antibody IgG and detection of the effect on ocular infection. The IgG fraction of monoclonal GLXA-Ab$_1$ or Ab$_3$ was incubated with elementary bodies of C. trachomatis serovar C. Normal mouse or rabbit pre-immune IgG as well as no immunoglobulin added served as controls. The mixture was inoculated to each eye of the primate. On the day before and after the inoculation, conjunctival swabs were taken by sweeping different areas of the conjunctivae (see above). Ocular chlamydial infection in primates was determined by cell culture assay which included second-passage on days post-infection. As shown in Table 1, three primates were infected with monoclonal GLXA-Ab$_1$ treated EBs on the left eyes, GLXA-Ab$_3$ treated EBs on the right. At the same time, two primates were infected with normal mouse IgG treated EBs (shown as NI) or EBs alone on the left and right eyes alternatively. The same method applied to pre-immune rabbit IgG (shown as N3). All eyes inoculated with monoclonal GLXA-Ab$_1$ treated EBs were positive at least once (primate No. 515, 84, and 26). However, only one eye of the GLXA-Ab$_3$ treated eye was positive once, at day 10 post-infection, two of them were never positive (primate No. 515, 84 and 26). Eyes inoculated with normal mouse or pre-immune rabbit IgG treated EBs were all positive at least once (primate No. 563, 20, 17 and 329). The untreated EBs (shown as C) produced infection in two of the four eyes involved (primate No. 563, 20, 17 and 329). Although the data points are diminutive, they do show that monoclonal GLXA-Ab$_1$ does not neutralize chlamydia in primate conjunctiva. On the other hand, it suggests that GLXA-Ab$_3$ is neutralizing. In order to confirm that GLXA-Ab$_3$ does neutralize, a number of tests were carried out, including: (A,) neutralization in cell culture (B), neutralization in primate conjunctiva (C), detection by clinical culture assay (D), detection by direct fluorescence antibody cytology (E), chlamydia specific RNA probe hybridization and (F) determination of the severity of ocular infection by clinical scoring.

TABLE 1

Neutralization of chlamydial infection in primate conjunctivae by Ab$_3$ but not mAb$_1$

| | | | Day Following Infection | | | | |
|---|---|---|---|---|---|---|---|
| Primate | Eye | Ab[a] | 0 | 3 | 7 | 10 | 14 |
| 515 | L | mAb$_1$ | – | – | + | + | – |
|  | R | Ab$_3$ | – | – | – | – | – |
| 563 | L | C | – | – | – | – | – |
|  | R | N$_1$ | – | – | – | + | – |
| 84 | L | mAb$_1$ | – | – | – | + | + |
|  | R | Ab$_3$ | – | – | – | + | – |
| 20 | L | N$_3$ | – | – | – | + | – |
|  | R | C | – | – | – | – | – |
| 26 | L | mAb$_1$ | – | – | + | – | – |
|  | R | Ab$_3$ | – | – | – | – | – |
| 17 | L | N$_1$ | – | – | – | + | + |
|  | R | C | – | – | – | + | + |
| 329 | L | C | – | – | + | – | – |
|  | R | N3 | – | – | – | + | + |

[a]EBS treated with normal mouse IgG(N1), pre-immune rabbit IgG (N3) or EBs alone (C) were controls.

GLXA-Ab$_3$ neutralizes the chlamydial infection in vitro

In vitro, cell culture assay was carried out with GLXA-Ab$_3$ and pre-immune rabbit antibody. The pre-immune rabbit and GLXA-Ab$_3$ (90MS699) IgGs were isolated by protein A affinity chromatography. The mixture of 10 ug of each IgG and 100 ul serovar C EBs (1000 IFU/ml) or EBs alone were inoculated onto wells containing McCoy cell monolayers. Ten wells per sample were used. Inclusion bodies were detected by FITC-conjugated monoclonal anti-chlamydia antibody 48 hours after the incubation. IFU/ml was based on 15 fields per well. As is shown in Table 2, Ab$_3$ IgG reduced the infectivity 3 times higher compared to pre-immune IgG, 5 times higher compared to EBs alone, indicating neutralization by GLXA-Ab$_3$.

TABLE 2

In vitro neutralization of chlamydial infection by Ab$_3$ IgG

| EBs treated with | Mean IEU/15 Fields + S.E.M |
|---|---|
| Ab$_3$ | 34.1 + 7.2 |
| Normal IgG | 93.8 + 22.4 |
| None | 155.3 + 5.5 |

GLXA-Ab$_3$ neutralizes the chlamydial infection in primates
Eight primates were randomly divided into three groups in this experiment. In the eyes, four primates received purified EBs previously incubated with GLXA-Ab$_3$ IgG (eight eyes), two received EBs previously incubated with pre-immune IgG (four eyes) and two received untreated EBs (four eyes). On the examining day, the conjunctival swabs were taken and cell cultured. Since there is no significant differences between the recipients of pre-immune IgG and EBs alone, the results are presented as 8 experimental eyes and 8 control eyes. Cell culture results are expressed as IFU/ml based on counting inclusions in 15 fields for two wells per sample. As shown in Table 3, 20 days after the challenge, 1 of eight eyes was positive compared to eight out of eight eyes that were positive in the control group. When the accumulated results were examined, with GLXA-Ab$_3$, 9 of 40 (22.5%) were positive, in contrast, 36 of 40 (90%) were positive without GLXA-Ab$_3$.

TABLE 3

Neutralization of chlamydial infection in primate conjunctivae by Ab$_3$ IgG by cell culture assay[a]

| Day of Experiment | No. of Eye Culture Positive | | | |
|---|---|---|---|---|
| IgG Control | Ab$_3$ | Preimmune | None[a] | Combined |
| 0 | 0/8 | 0/4 | 0/4 | 0/8 |
| 2 | 3/8 | 2/4 | 3/4 | 5/8 |
| 6 | 3/8 | 4/4 | 4/4 | 8/8 |
| 9 | 1/8 | 3/4 | 4/4 | 7/8 |
| 12 | 1/8 | 4/4 | 4/4 | 8/8 |
| 20 | 1/8 | 4/4 | 4/4 | 8/8 |
| | 9/40 | 17/20 | 19/20 | 36/40 |

[a]Only one first passage negative sample was second-passage positive.
bEBs were previously incubated without antibody.

In a parallel assay, direct fluorescence antibody cytology assay (DFA) was also carried out to evaluate the numbers of EBs from the conjunctival swabs. The conjunctival swab samples were fixed onto slides and stained with FITC-labeled monoclonal antibody against *C. trachomatis*. It was considered to be positive when 5 or more characteristic elementary bodies were seen on each slide (Micro Trak, Syva Co. CA). As shown in Table 4, EBs were detected in the GLXA-Ab$_3$ treated group on only two occasions, day 6 and 12 post-infection, while the remainder were positive through day 20. Only one eye was EB negative in the non-treated group up at day 2, that was probably an artifact. EBs were detected in all eyes in this group for the remainder of the experiment. On the last examination day (day 20), none of the eyes treated with GLXA-Ab$_3$ was positive, while 8 of 8 were positive in the combined control group. In addition, DFA and culture results are completely congruent.

TABLE 4

Neutralization of chlamydial infection by Ab$_3$ using direct fluorescence antibody cytometry assay (DFA)[a]

| Day of Experiment | No. of Eye Culture Positive | | | |
|---|---|---|---|---|
| | Ab$_3$ | Preimmune IgG | None[b] | Combined Control |
| 0 | 0/8 | 0.4 | 0/4 | 0/8 |
| 2 | 0/8 | 2/4 | 3/4 | 5/8 |
| 6 | 1/8 | 2/4 | 4/4 | 6/8 |
| 9 | 0/8 | 4/4 | 4/4 | 8/8 |
| 12 | 1/8 | 4/4 | 4/4 | 8/8 |
| 20 | 0/8 | 4/4 | 4/4 | 8/8 |
| | 2/40 | 16/20 | 19/20 | 35/40 |

[a]DFA was considered positive if 4 EBs were found on a slide.
[b]EBs were considered previously incubated without antibody.

Figure 8:
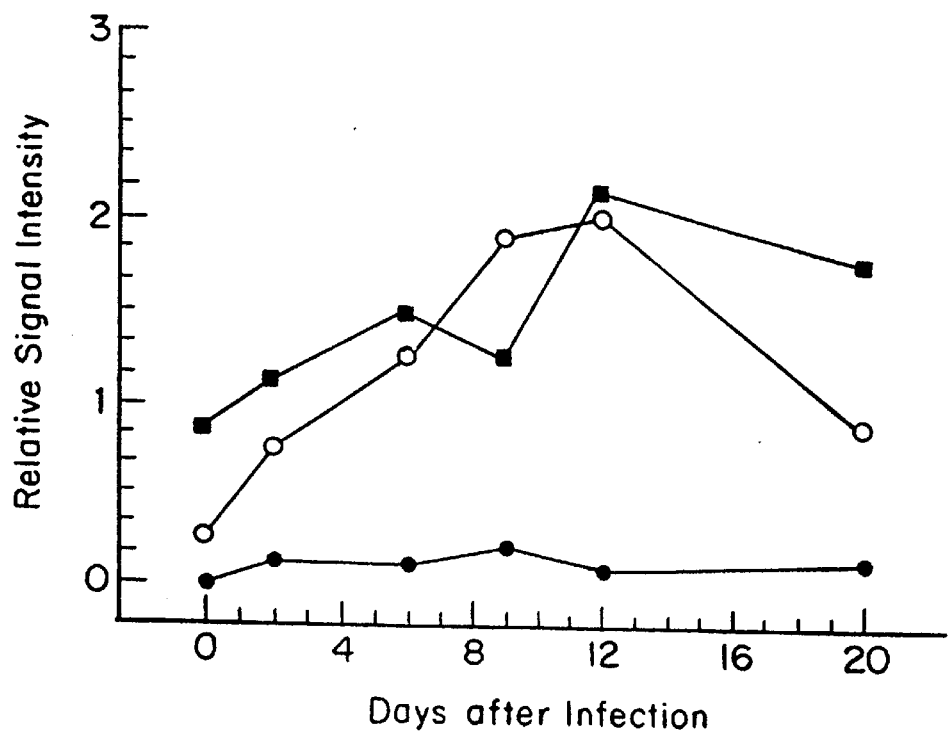
FIG. 8 is a curve showing the detection of chlamydial specific ribosomal RNA from primates.

GLXA-Ab$_3$ substantially attenuates the chlamydial replication in conjunctival infection
To further understand the mechanism of the neutralization, chlamydial specific ribosomal RNA had been examined from those primate conjunctival swabs by a DNA probe (Cheema et al, The Ameri. J. Med. Sci. 302:261–268, 1991). Total RNA was extracted from conjunctival swabs taken from primate eyes. RNA from serovar C EBs, human or yeast were used as control. $^{32}$P-chlamydial DNA encoding ribosomal RNA16S and 23S genes was used to detect chlamydial specific RNA in a Northern slot-blot hybridization assay. As shown in FIG. 8, control eye (infected either with pre-immune rabbit IgG plus EBs or EBs alone) uniformly show significant levels of chlamydial RNA at all time points examined, similar RNA samples prepared from the eyes of GLXA-Ab$_3$-treated organism show significantly attenuated levels of chlamydial RNA Chlamydial ribosomal RNA was extracted from conjunctival swabs from four primates infected with Ab$_3$ IgG (●) treated Ebs, two with pre-immune rabbit IgG (○) treated and two with EBs alone (■). Relatively signal intensity from Northern slot-blot autoradiograms is expressed by using an arbitrary scale. Means were derived from values for each of the two eyes of each primate at the time point. This indicates that the neutralization happens at the very early stage of the infection.

Figure 9:
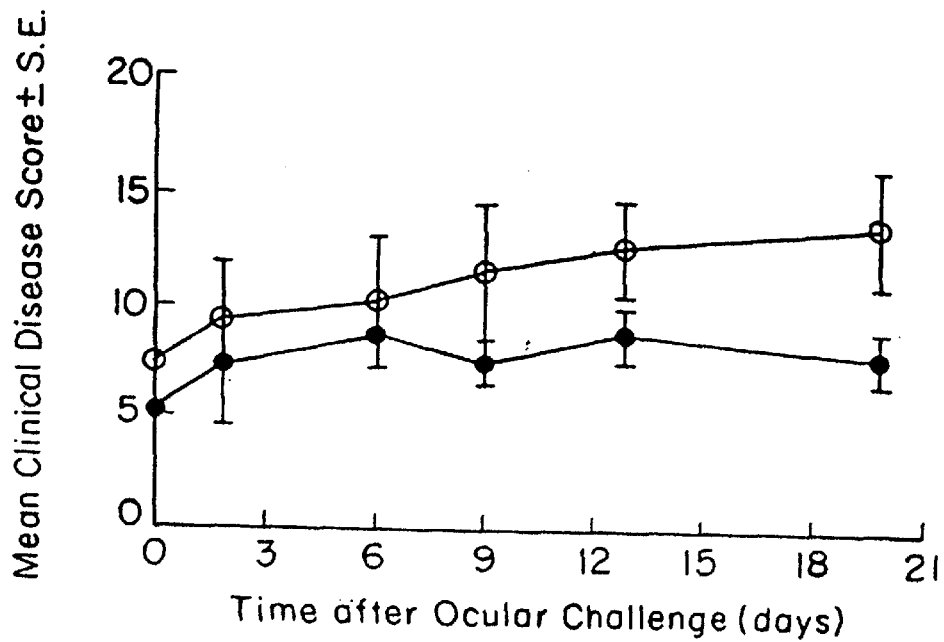
FIG. 9 is a curve showing the effect of GLXA-$Ab_3$ IgG on ocular infection by clinical disease score.
Figure 10:
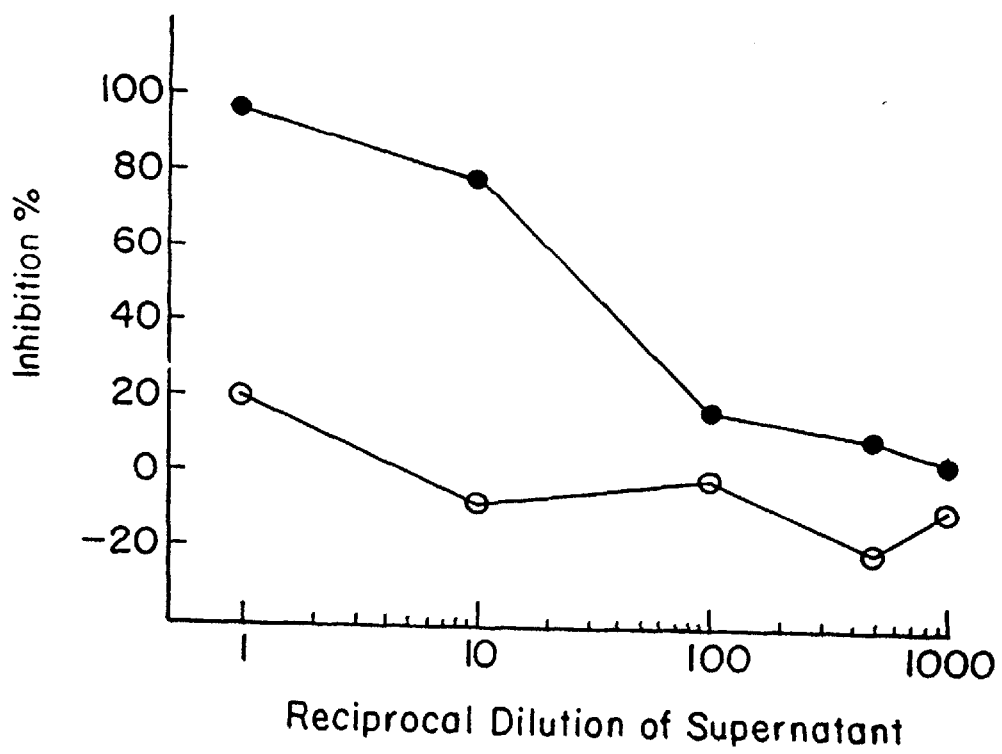
FIG. 10 is a curve showing the inhibition of bending of monoclonal GLXA $Ab_1$, to GLXA by a hybridoma clone.
Figure 11:
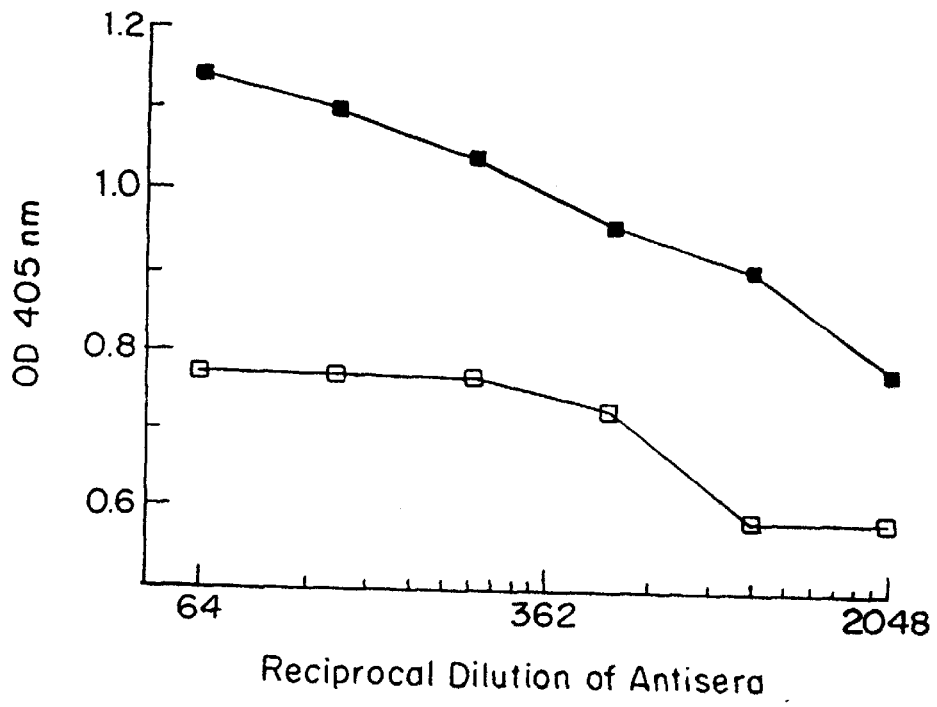
FIG. 11 is a curve showing the direct binding of chlamydia patient antiserum to monoclonal GLXA-M $Ab_2$.
Figure 12:
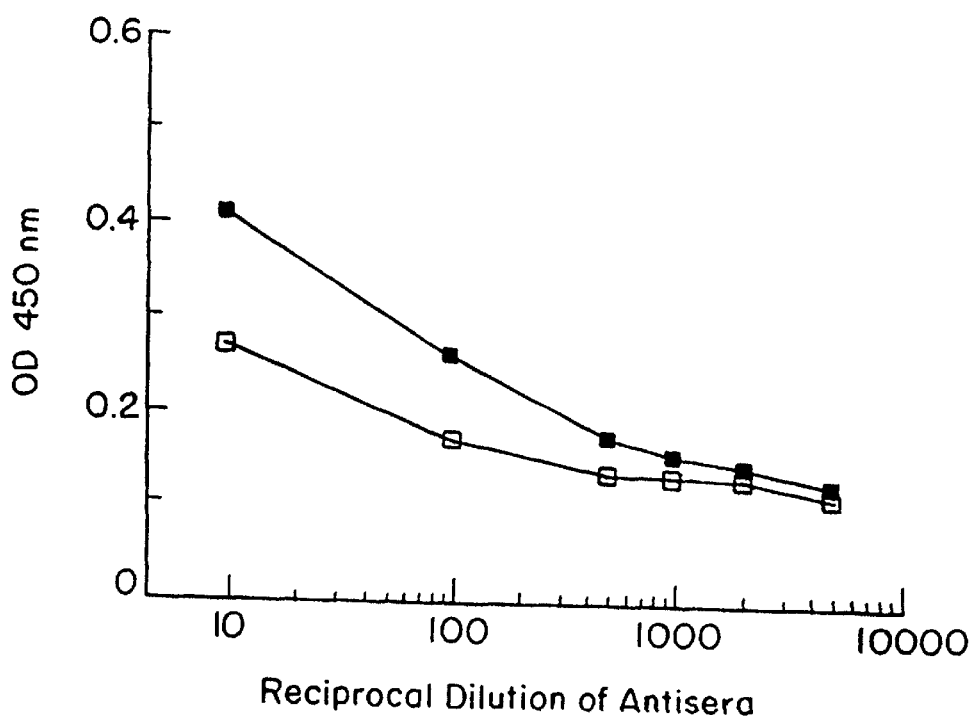
FIG. 12 is a curve showing that rabbit anti-chlamydia antiserum recognizes monoclonal GLXA-M $Ab_2$.

The degree of conjunctival inflammation after inoculation with EBs previously incubated with either GLXA-Ab$_3$ or pre-immune IgG or without previous incubation was evaluated by clinical response. The clinical response was graded based on a total clinical disease scores (TCDS) derived from 10 clinical features of inflammation (Taylor et al, Invest. Opthalmol. Vis. Sci. 29:1847, 1988). The accumulative disease scores were obtained for each group of primates by examining 10 signs existing in the conjunctiva. Clinical disease scores was graded on the scale of 0 to 3 for each 10 signs of conjunctiva inflammation. Total inflammation scores was obtained from each primate infected with Ab$_3$ (●) treated or pre-immune rabbit IgG (○) treated elementary bodies. As shown in FIG. 9, recipients of GLXA-Ab$_3$ developed very little clinical disease and this declined after day 8. Control animals continued to develop severe disease through day 21 post-challenge. This pathological finding is consistent with cell culture, DFA and RNA hybridization data.

Generation of And Characterization of Hybridoma Cell Lines Producing Anti-idiotypic Antibody Production of anti-idiotypic hybridoma cells Five syngeneic mice (BALB/cByJ) were immunized intraperitoneally with KLH conjugated monoclonal GLXA-$Ab_1$ IgG in the presence of Freund's complete adjuvant. The anti-idiotypic anti-sera against monoclonal GLXA-$Ab_1$ IgG from these mice were detected by sandwich ELISA. The titer was about 1:1000 three weeks after the immunization (data not shown). Fusions were made between Sp2/0-Agl4cells and spleen cells from two mice which had the highest titer against monoclonal GLXA-$Ab_1$. The size of the spleens was almost twice the size of a normal spleen. The clones were screened by the same method for mouse antisera testing. The pool of mice antisera or pre-immune sera diluted 1:10 was used as controls in all screening tests. Among 283 wells screened, 8 were considered positive against mAbl with a titer two times or higher than negative control. These hybridomas were cloned. One clone (91 MS441) had the highest titer in ELISA and was propagated. The ascites was produced and IgG isolated. The isotype of IgG of this clone was identified to be IgGl, having a K light chain (Bio-Rad Laboratories, CA). The fusion results was summarized in Table 5.

lated monoclonal GLXA-$Ab_2$ IgG was coated on a microtiter plate and tested for reactivity with the patient's serum (91 MS253) by ELISA. Human serum without clinically diagnosed chiamydial infection (88MS356) was used as a negative control. The results showed that the patient's serum had a titer which was more than 1:2000 against monoclonal GLXA-$Ab_2$ (FIG. 11). The test was carried out by ELISA. Serial dilutions of the antiserum obtained from a patient diagnosed as chlamydial infection (■) and non-diagnosed individual (□) were incubated with $mAb_2$ IgG coated on the polystyrene wells. The second antibody is goat anti-human peroxidase conjugate. Data is then presented as means of duplicates. This demonstrates that infected human antisera has the specific antibody against monoclonal GLXA-$Ab_2$, implying that monoclonal GLXA-$Ab_2$ is the internal image of GLXA.

The specific recognition of monoclonal GLXA-$Ab_2$ by a rabbit anti-chlamydial antisera (88MS188) was also tested in the similar way. The rabbit antiserum was produced by inoculating EBs. As shown in FIG. 12, rabbit antisera has higher binding to monoclonal GLXA-$Ab_2$ than pre-immune serum, but lower than expected. The difference between the binding is seen to the dilution factor of 1:1000. Polystyrene plate was coated with $mAb_2$IgG, 1 ug/well. Serial dilutions of rabbit antiserum specific to chlamydial EBs (■) or pre-immune rabbit serum (□) were added to each well in duplicate. The specific binding of the antiserum was

TABLE 5

Summary of fusion for anti-idiotypic antibodies

| Immunized BALB/cByJ Mice | Anti-di Titer in Supernatent | Total Wells with Growing Hybridoma | (%) | Wells Stable Postive of Anti-id | (% of Total) | Cloned Anti-id Lines |
|---|---|---|---|---|---|---|
| 2 | 1:1000 | 283 | | 8 | | 1 |
| | | | (2.8) | | (0.35) | |

Light chain: K
Heavy chain: $IgG^1$

Hybridoma (91MS441) secreting IgG inhibits the binding of monoclonal GLXA-$Ab_1$ to GLXA The supernatant from positive clones were further tested for the inhibition of the binding of monoclonal GLXA-$Ab_1$ to GLXA by chemiluminometric immuno-assay. Total inhibition of the binding was found from the supernatants of 4 clones without dilution. Two weeks later only one clone (91 MS441) was found stable. As shown in FIG. 10, at a dilution of 1:10, the supernatant from this clone inhibits the binding of monoclonal GLXA-$Ab_1$ to GLXA by 80% compared to 0% of a non-positive clone (91 MS442) from the same fusion. Serial dilutions of culture supernatant from clone 91MS441 (●) and negative clone 91MS442 (○) were tested by chemiluminometric immunoassay. The percent is obtained from the mean of the duplicate. This demonstrates that an anti-idiotypic clone was produced. It is identified as monoclonal GLXA-$Ab_2$. Monoclonal GLXA-$Ab_2$ is recognized by patient and rabbit anti-chlamydia antisera.

As an internal image of an antigenic determinant, the anti-idiotypic antibody should be recognized by any specific antisera which is against this epitope regardless of species. In order to test this property of the IgG produced by clone 91 MS441, human serum from a patient clinically diagnosed as chlamydia positive was used. Since the isotype of monoclonal GLXA-$Ab_2$ is IgGl, the purification of the IgG was carried out by protein G affinity chromatography. The isodetected by mouse anti-rabbit IgG (H&L) HRP conjugate and TMB substrate. This shows that rabbit antiserum which is against chlamydia has the specific antibody recognizing monoclonal GLXA-$Ab_2$, an additional evidence for monoclonal GLXA-$Ab_2$ as an internal image.

Antisera monoclonal GLXA-$Ab_3$ from syngeneic mice recognize GLXA

The anti-idiotypic antibody as an internal image can raise antigen specific antisera in animals that have never been exposed to that antigen. In this case, if monoclonal GLXA-$Ab_2$ (91 MS441) is the internal image of GLXA, (that is bearing the same antigenic structure), it should produce an anti-GLXA antibody in the same strain BALB/c ByJ mice in spite of the fact that they have never been exposed to GLXA. In an initial experiment, 8 mice were immunized with monoclonal $Ab_2$ IgG, four mice with normal mouse IgG. No adjuvant was used in the subcutaneous injection. Seven days and 14 days after the immunization and one boost, antisera were obtained from these mice by sacrificing half of the mice in each group. Immuno-dot blot assay was carried out with purified GLXA. The dot blot showed that mice immunized with monoclonal GLXA-$Ab_2$ IgG had a titer as high as 1:800 compared to 1:100 or less of the mice immunized with normal mouse IgG. The blots were further quantified by a densitometer. When diluted to 1:100 after the first boost, the antisera from all four mice bind to GLXA whereas no binding was seen in the control group even when diluted 1:50. This demonstrates that this antisera is solely elicited by the paratope of the anti-idiotype because the recipients are syngeneic.

GLXA-Ab$_3$ from syngeneic mice inhibits the binding of monoclonal Ab$_1$ to GLXA GLXA-Ab$_3$ antisera which specifically bind to GLXA were also tested for the inhibition of the binding of monoclonal Ab$_1$ to GLXA by chemiluminometric immunoassay. At a dilution of 1:25, GLXA-Ab$_3$ inhibits 90% of the binding compared to 18% of inhibition by the control antisera day 8 post immunization. This is equal to the same inhibition demonstrated by 10 ug of unlabeled monoclonal GLXA-Ab$_1$. The same inhibition was found in the antisera on day 14, one week after the first boost with the same amount (50 ug/mouse) of IgG. It is noted that inhibition percentage dropped from 70% on day 7 to about 50% on day 14 when diluted 1:100.

Figure 13:
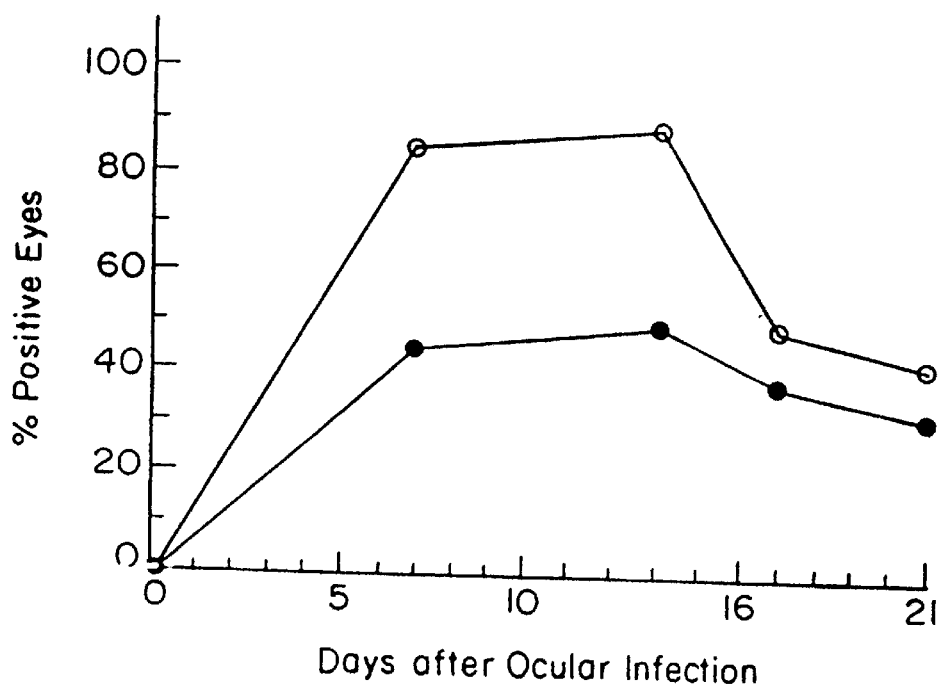
FIG. 13 is a curve showing the protection of mice from chlamydial infection by immunization with monoclonal GLXA-M $Ab_2$.
Figure 14:
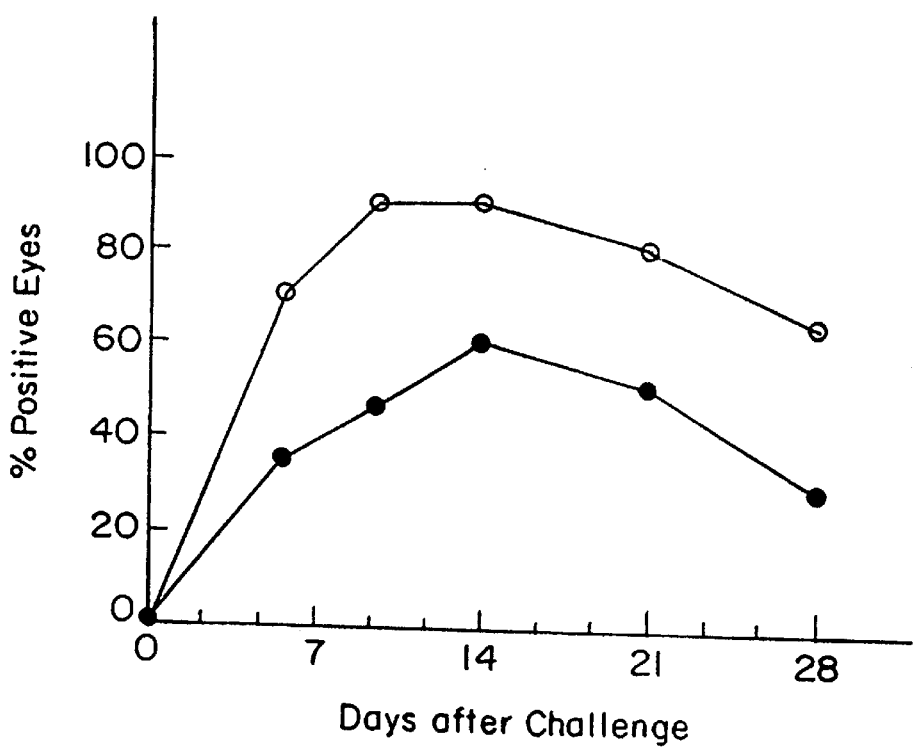
FIG. 14 is a protection curve by monoclonal GLXA-M $Ab_2$ IgG after a high dose of ocular infections.

Immunization with Monoclonal GLXA-Ab$_2$ Protects Mice from Chlamydial Infection BALB/c ByJ mice were used as an ocular chlamydial infection animal model in this study. The first experiment was carried out with 39 mice. Twenty mice were immunized subcutaneously with 50 ug of monoclonal GLXA-Ab$_2$ and nineteen with normal mouse IgG without any adjuvant. They were given a total of three injections, one week apart. One week after the last injection, the mice were inoculated with C. trachomatis serovar C elementary bodies (5000 IFU in each eye). The conjunctival swabs were taken from each eye of the mice on day 0, 7, 14, and 21 post infection. Samples from conjunctival swabs were collected and cultured in McCoy cell monolayers for 48 hours. Inclusion bodies were counted, and 5 inclusions were considered as positive in 15 fields. As shown in FIG. 13, mice immunized with monoclonal GLXA-Ab$_2$ had half the infectivity compared with mice immunized with normal mouse IgG. In a second experiment (twenty mice in each group), the immunization was repeated in the similar manner. However, they received $10^6$ IFU per eye, 100 times the number of EBs as used in the first experiment. Twenty mice were immunized with mAb$_2$ (●) and nineteen with normal mouse IgG (○) subcutaneously (50 ug IgG/mouse). They were ocular challenged with C. trachomatis serovar C. EBs after three times immunization in a week interval. Each eye received 5000 IFU. One day before and after the challenge, conjunctival sample was taken from each eye and cell cultured. Percentage of positive eyes are based on the number of the positive eye among all the eyes examined in a group. Surprisingly, almost the same protection curve found in the mice (FIG. 14), suggesting that monoclonal GLXA-Ab$_2$ elicits a vigorous host defense response. After immunization three times in a week interval, twenty mice immunized with mAb$_2$ IgG (●) and twenty with normal mouse IgG (■) received approximate $5\times10^4$ to $5\times10^6$ chlamydia trachomatis serovar C. EBs per eye. Conjunctival chlamydial inclusions were tested by cell culture obtained from conjunctival swabs. Values are the means of first and second passage culture except day 28.

Figure 15:
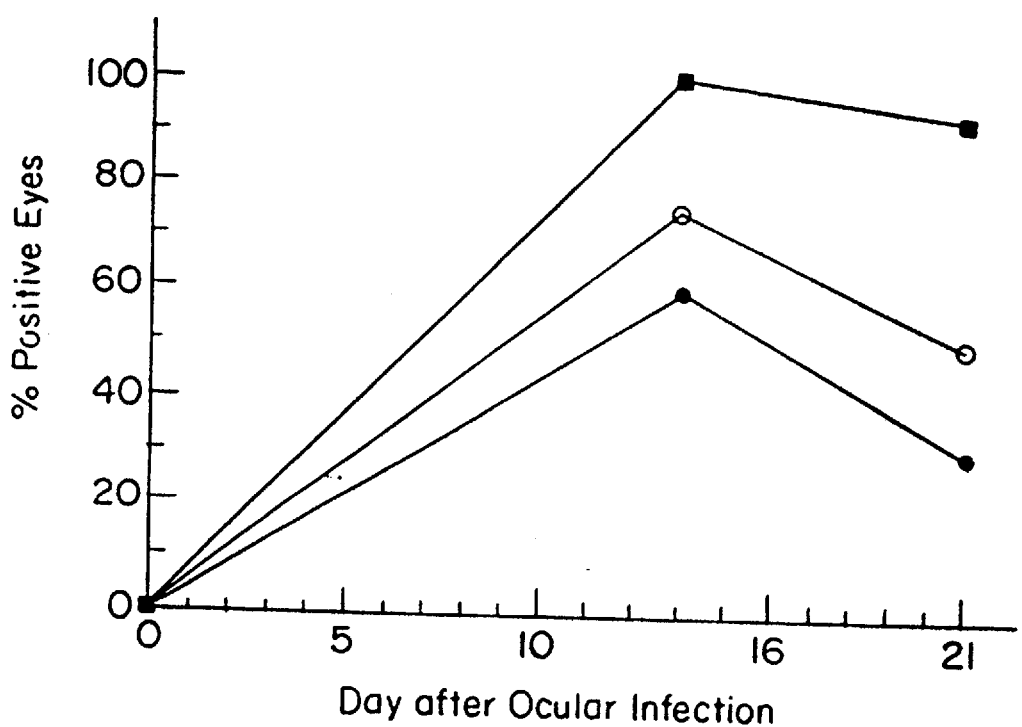
FIG. 15 is a curve showing the effect of alum on the protection of mouse chlamydial infection.
Figure 16A:
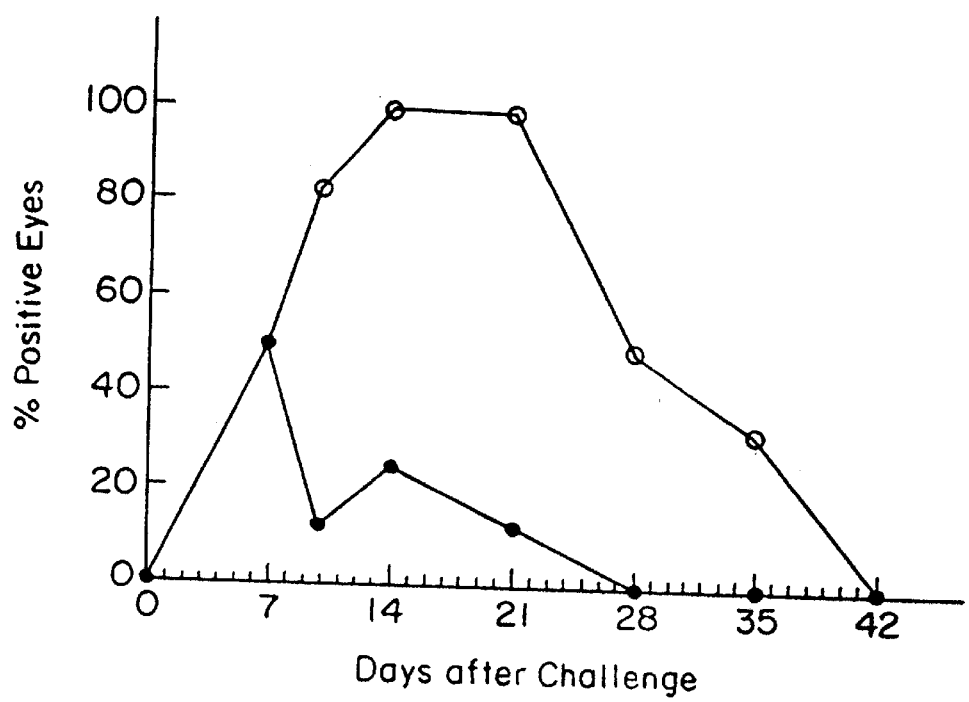
FIGS. 16A and 16B show curves of the time course of ocular infectivity after immunization with monoclonal GLXA-$Ab_2$.
Figure 16B:
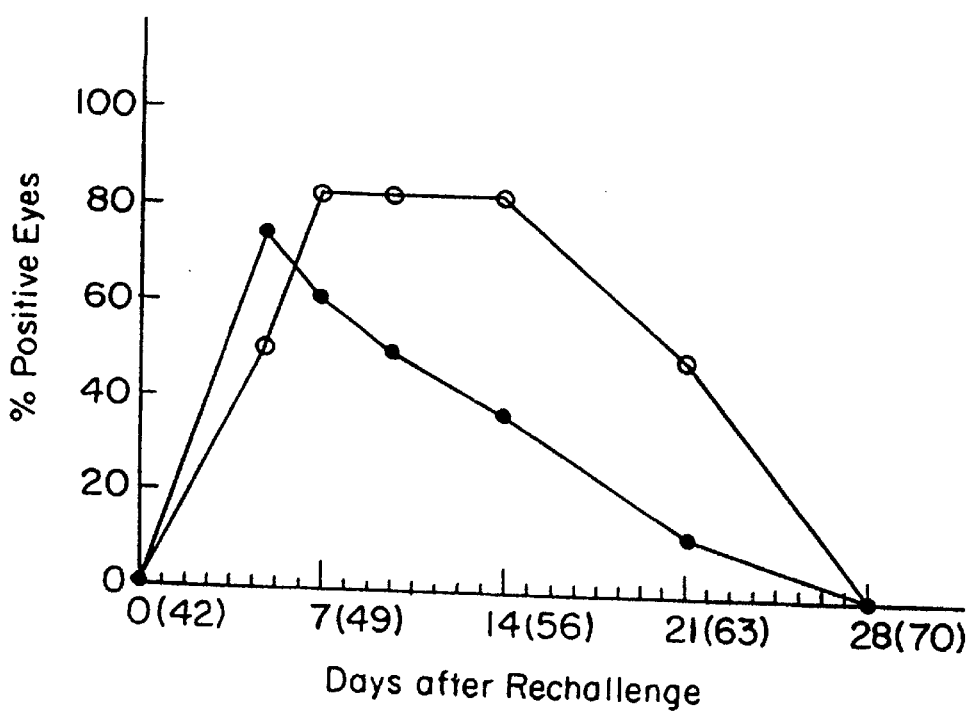

In a third experiment, aluminum hydroxide (alum) was used in the immunization. Ten mice were immunized with monoclonal GLXA-Ab$_2$ in the presence of Maalox as adjuvant, eight mice immunized without Maalox and sixteen mice immunized with normal mouse IgG in the presence of Maalox. The immunization procedure is the same as the previous ones. When Maalox was used in the immunization, the titer of the anti-anti-idiotypic antisera in mice was doubled as tested against GLXA in immuno-dot blot. The higher titered antisera in the adjuvant treated mice demonstrate more effective protection in the mice from the ocular infection compared to the ones immunized without alum (FIG. 15). Ten mice were immunized with mAb$_2$ IgG plus alum (●), eight with mAb$_2$ IgG without alum (○) and sixteen with normal mouse IgG plus alum (■). One week after the last boost, mice were ocularly infected and conjunctival infection was detected by cell culture on day as shown. However, mice immunized with monoclonal GLXA-Ab$_2$ had significantly less infection than those receiving normal mouse IgG plus alum. In addition, the infection was cleared by post challenge day 28. In the fourth experiment, eight mice were immunized with monoclonal GLXA-Ab$_2$ and eight with normal mouse IgG in the presence of alum. The immunization and inoculation protocols are the same as before. However, as shown in FIG. 16(A), on day 7, both groups had the same degree of infection, 50% of the eyes are infected. However, beginning on day 10, a significant difference of the infection is seen between the two groups. For the group immunized with monoclonal GLXA-Ab$_2$ IgG, on day 14, two out of eight eyes were positive. On day 22, one out of eight. No eye was positive on day 28, showing a clear regression of the infection. In contrast, mice immunized with normal mouse IgG, on day 14, six out of six eyes were positive and continued to be positive until day 42. The number of infected eyes began to fall by day 28 seen in this group is believed to be a natural recovery process. In a final experiment, the mice with completely cleared infection from the above experiment were rechallenged with EBs in order to evaluate whether the immunity was associated with memory. A significant factor in terms of protection is the ability of the immunized mice to clear the organisms from their eyes much earlier than the non-immunized ones. This is clearly shown to be the case with mice immunized with monoclonal GLXA-Ab$_2$ (FIG. 16(B)). This shows that monoclonal GLXAAb$_2$ not only is able to evoke a protective immune response but also a memory immune response. After immunization three times in a week interval, twenty mice immunized with mAb$_2$ IgG (●) and twenty with normal mouse IgG (○) received approximate $5\times10^4$ to $5\times10^6$ chlamydia trachomatis serovar C. EBs per eye. Conjunctival chlamydial inclusions were tested by cell culture obtained from conjunctival swabs. Values are the means of first and second passage culture except day 28.

This example illustrates that an anti-idiotypic antibody which mimics GLXA, protects mice, as an animal model, from chlamydial ocular infection. The monoclonal antibody mAb$_1$ (89MS30) which was used to produce anti-idiotypic antibodies was produced by immunization with whole EBs and screened for its reaction to a genus specific antigen. It has been used to identify GLXA and demonstrated specific binding to the polysaccharide portion of GLXA. This antibody was also found cross-reactive to cLPS.

First GLXA and cLPS are distinctly different genus specific antigens. GLXA was found on RBs, EBs, inclusion membranes, host cell membranes and shed into the inclusion space, cytoplasm of the infected cells and into the surroundings. It was obtained from the supernatant of infected cell culture. Whereas cLPS was found both on EBs and RBs (mainly Rbs), cLPS is not secreted or shed from infected cells, but loosely bound to the RBs. Structurally, they have different polysaccharide moieties. GLXA has a unique sugar residue: gulose or gulose derivatives, mannose and galactose, probably arranged in repeating units of guluoronic and mannuronic acids. Only two fatty acids were found associated with the antigen compared to at least in 12 cLPS. Whereas cLPS has typical linear 2-keto-3-dexyoctonoic acid (KDO) trisaccharide (common core) and polysaccharides like glucosamiane and heptose. Serologically, monoclonal GLXA-Ab$_1$ specifically bind to gulose and mannose repeating block. Whereas, cLPS genus specific epitope is on KDO, the specific determinant is the 2–8 linkage. Obviously, it is very unlikely that GLXA and CLPS share the same epitope. It is known that antibodies, whether poly-or monoclonal, antibodies produced either by immunization with whole EBs or with purified cLPS, which are specific to cLPS, have no neutralizing or protective functions. From the composition analysis, it is suggested that gulose together with mannose and galactose form the specific epitope of GLXA. Whereas, cLPS, in addition to KDO trisaccharide as an epitope, has other epitopes in KDO region and also other saccharide portions. These later structures have shown a broad cross-reaction with LPS from other gram negative bacteria. Since the protective epitope of GLXA consists of an array of sugar residue, it is more reasonable to believe that some of which cLPS is partially shared with GLXA.

There are some other possibilities regarding this cross-reaction. For example, (1) GLXA and cLPS do not share any primary similarity, but structurally form similar binding motif; (2) although monoclonal GLXA-Ab$_1$ binds to cLPS, GLXA and cLPS do not have a similarity in antibody binding site. The monoclonal antibody can be multispecific, that is, it can recognize a quite different epitope.

From the discussion above, it is believed that monoclonal GLXA-Ab$_1$ is specific to GLXA epitope, the possibility that GLXA and cLPS share some sugar residues or merely structure similarity may explain the cross-reactivity.

Anti-idiotypic antibodies, GLXA-Ab$_3$ and monoclonal GLXA-Ab$_2$

Anti-idiotypic antibody is a potent and long lived immunogen

Monoclonal GLXA-Ab$_1$ was injected into guinea pigs subcutaneously in the absence of conjugate or Freund's adjuvant. All four immunized guinea pigs developed high titered anti-idiotypic antibodies specific to monoclonal Ab$_1$, which were found as early as 3 weeks after the first immunization. The titer was approximately 1:5000 by ELISA. The anti-idiotypic antisera produced contained a relatively high concentration of GLXA-Ab$_2$ which is specific to the hypervariable region of monoclonal GLXA-Ab$_1$. This was shown after two absorptions by normal mouse IgG. When the IgG1 isotype from guinea pig anti-idiotypic antibodies was used as an immunogen in three rabbits, the titer of anti-anti-idiotypic antibody was more than 1:20,000 two months after immunization. This demonstrates that immunoglobulin itself is a very potent immunogen. This is true not only for interspecies immunization, but also syngeneic immunization. With monoclonal anti-idiotypic antibody monoclonal GLXA-Ab$_2$, the immunization was carried out in syngeneic mice without KLH-conjugation or Freund's adjuvant. The mice developed high titered GLXA-Ab$_3$ in a short time after immunization (9 days). The protocol used in this study is different from most methods which use either a conjugate or Freund's adjuvant for a higher immunogenicity. This indicates that immunoglobulin as an antigen is more immunogenic compared to most isolated or synthetic peptide antigens.

A successful vaccine not only requires that it be a good immunogen but that it is long lasting (preferably for the lifetime off the host). The immunity produced by idiotype is long lived. The ability to inhibit the binding of monoclonal GLXA-Ab$_1$ to GLXA by guinea pig GLXA-Ab$_2$ from three immunized guinea pigs have been monitored for as long as 77 weeks. With only three boosts, the inhibition one year post immunization is almost equal to antisera collected in the early stages after the immunization. This indicates that the immunity elicited by the idiotypic antibody monoclonal GLXA-Ab$_1$ has a long term memory. Since the half-life of an antibody molecule or the majority of antibody-producing cells is about a few weeks, the boosting interval (six months) is far beyond the life span of the B cells and the immunoglobulins. It is the constant stimulation within the idiotypic network that keeps this anti-idiotypic antibody at a certain level. The change of idiotypic specificity during this period has not been seen in this case.

An internal image of chlamydial GLXA, isotypic difference

In this study, guinea pig GLXA-Ab$_2$ IgG1 and IgG2 were separated. The regulatory function of these two isotypes to the idiotype was not evaluated. However, the difference between IgG1 and IgG2 subclasses have been found in inhibition of the binding of monoclonal GLXA-Ab$_1$ to GLXA. With a novel system, chemiluminometric immunoassay, the incubation and the final detection were all carried out in solution rather than solid phase as in ELISA, thus greatly lessening the possibility of the inhibition by hindrance. The results have shown that GLXA-Ab$_2$ IgG1 inhibited 100% of the binding whereas IgG2 50% at the same concentration. This suggested that GLXA-Ab$_2$ IgG1 has a high affinity in binding to the idiotype or being more like the antigen, GLXA. This demonstrates an isotypic difference in their binding ability to the idiotype which reflects a difference in their respective active sites. IgG1 has a different idiotype binding ability from IgG1. There are a number of examples of dominant idiotypes, for example, A5A idiotope of anti-strep-A carbohydrate antibodies or the T15 idiotope of phosphoryl choline antibodies. It is not clear if there is any isotype preference of anti-idiotypic antibody in different systems. This finding suggests that a certain isotype of GLXA-Ab$_2$ is the internal image while others are not.

Monoclonal GLXA-Ab$_2$ as an immunogen of chlamydial GLXA

The purpose of making monoclonal anti-idiotypic antibodies is to: (1) have a constant source of anti-idiotypic antibody for vaccine study; (2) identify a possible receptor for GLXA on host cells; and (3) further characterize the epitope on GLXA. This enables an understanding of biological functions of GLXA in terms of epitope density, its role in mechanism of infection and the protective function against chlamydial infection in vivo. The production of monoclonal anti-idiotypic antibodies was carried out in the syngeneic BALB/cBYJ mice. In the first fusion, one stable, highly inhibitory clone (91MS441) from 283 clones screened was selected. In the second fusion, another clone (91MS442) was selected though it is not as inhibitory as 91MS441 clone in chemiluminometric immunoassay. The monoclonal GLXA-Ab$_2$ produced by this clone (91MS441) has been shown to be the internal image of the chlamydial antigen, GLXA.

It is interesting to note that the inhibitory ability of mouse GLXA-Ab$_3$ slightly but obviously decreases over time. The dosage of the anti-idiotype has been a factor in either enhancing the idiotype or suppressing the idiotype. This inhibition results by GLXA-Ab$_3$ has shown that after administration of monoclonal GLXA-Ab$_2$IgG twice, the inhibition is higher than the sera obtained after administration three times. This indicated 50 ug is either too much for one dose or too much for repeated administrations. On the other hand, it also shows that a low amount is enough for protective immunity. The reason for choosing normal mouse IgG as a negative control in the immunization rather than a nonrelative clone is that it would prevent any possible bias from a specific clone.

Monoclonal GLXA-$Ab_1$ and GLXA-$Ab_3$ bear the same antigen binding structure

GLXA-$Ab_3$ from immunized rabbits and mice recognized affinity purified GLXA by immuno-dot blot assay, though there is no previous exposure to GLXA or infection. The binding of monoclonal GLXA-$Ab_1$ to GLXA is inhibited as the concentration of GLXA-$Ab_3$ increases. This indicates that the anti-anti-idiotype has equivalent antigen reactivity as idiotype, that is they recognize the same epitope. The same antigen reactivity of monoclonal GLXA-$Ab_1$ and GLXA-$Ab_3$ from rabbits to GLXA was further proved in the immuno-fluorescent staining of the inclusions in infected McCoy cell culture. The experiment suggested the structural similarity of antibodies. Using monoclonal GLXA-$Ab_2$, which mimic GLXA, to identify its role would be valuable in understanding the mechanism of anti-idiotype protection. The experiment was carried out with human epidermoid carcinoma cells (A431) as well as human endometrial gland epithelial cells (HEGEC). Those cell lines were used because of their human origin. A preliminary binding experiment was performed by direct antibody staining detected with FACScan (Becton Dicknson, N.J.) flow cytometry. Since the separation of these epithelial cells into a single cell suspension is very difficult without using enzyme or harsh separation, especially HEGEC cells, the cell population consists of singlets, doublets and multiplets. Single cell population was gated right above the cell debris. Since the control, cells stained with normal mouse IgG was at exactly the same gate, it is believed that the two groups are comparable. In addition, the binding is direct, monoclonal GLXA-$Ab_2$ or normal mouse IgG was directly biotin labeled. The intensity of monoclonal GLXA-$Ab_2$ bound specifically to the host cells (HEGEC) increases as the antibody concentration increases. Normal mouse IgG has no such binding even at the highest concentration. If this finding can be repeated and proved to be valid, GLXA is an adhesin or a ligand which binds to HEGEC cells. There are some reasons to believe that GLXA is an adhesin or a ligand. First, as mentioned above, GLXA-$Ab_3$ neutralization occurs at the very early stage. This is proved by finding apparently no significant chlamydial specific ribosomal RNA in conjunctiva samples taken from primates inoculated with GLXA-$Ab_3$ treated EBs. This suggested that GLXA-$Ab_3$ blocked EBs from getting into the host. Second, GLXA was found to enhance the infection by approximately three fold when McCoy cells were pre-incubated with GLXA. It is only if GLXA as an adhesin or ligand which facilitate the attachment of EBs to host cells that this result can occur. Actually, EBs may well use this mechanism to infect host cells because GLXA is secreted from infected cells.

A possible mechanism of the role of GLXA may be the following: EBs attach to the host cells either by GLXA on EBs or by free GLXA which was secreted by the infected cells into the surroundings. This makes it much easier and efficient for GLXA to absorb to surrounding cells. EBs can then attach to the host cells either by GLXA on EBs, thus binding to the host cells. This mechanism seems much more efficient than a one to one attachment.

Neutralization of chlamydial infection by GLXA-$Ab_3$

The preliminary neutralization test in vitro has shown that more chlamydial inclusions were found with GLXA-$Ab_1$ treated than rabbit $Ab_3$ treated *C. trachomatis* serovar B EBs. This showed that GLXA-$Ab_3$ neutralized the infection, whereas monoclonal GLXA-$Ab_1$ did not. GLXA-$Ab_3$ neutralized the infection in cell culture whereas monoclonal GLXA-$Ab_1$ did not. This in vitro result was repeated in vivo in two later experiments with the primate infection model. It was confirmed that GLXA-$Ab_3$ effectively neutralized chlamydial infection both in vitro and in vivo.

The understanding of the mechanism of this neutralization comes from the chlamydia specific RNA hybridization experiment. The primates were ocularly inoculated with GLXA $Ab_3$ or normal rabbit IgG treated EBs. Chlamydial RNA was detected from the conjunctival swabs taken from primates on different days prior and post inoculation. The RNA hybridization assay used in this study is an extremely sensitive way to detect chlamydial infection in samples which are unequivocally negative by either cell culture of DFA or both. The substantially low RNA found in $Ab_3$ treated primates provides the evidence that the neutralization occurs at very early stage of the infection, before the internalization of the organisms. This suggests that GLXA may be an adhesin or ligand functioning at the stage of attachment.

The role of humoral immunity in protection against chlamydial infection has long been discrepant. However, it has been shown both in vitro and in vivo that humoral immunity may play some role in preventing chlamydial infection.

Protection of Mice from chlamydial infection by immunization with monoclonal GLXA-$Ab_2$ The chlamydial ocular infection model in BALB/cByJ mouse was employed in a vaccine study with monoclonal anti-idiotypic antibody monoclonal GLXA-IgG. It is a model for *C. trachomatous* serovars which only infect humans. In the immunization experiments, monoclonal (GLXA-$Ab_2$) IgG (50 ug/mouse) was used to immunize 6 to 20 mice in each group subcutaneously either in the presence of adjuvant or with no adjuvant. Mice immunized with monoclonal GLXA-$Ab_2$ mount a distinctive GLXA-$Ab_3$ titer detectable one week after a single immunization. The system used in this study is syngeneic: monoclonal GLXA-$Ab_1$, monoclonal GLXA-$Ab_2$ or GLXA-$Ab_3$ are all produced in the same strain of mice. They bear the same immunoglobulins genetically. The only "foreign structure" is the specific binding site of each type antibody (monoclonal GLXA-$Ab_1$ or monoclonal GLXA-$Ab_2$). Normal mouse IgG from the same strain was used as a negative control. Consistently, mice immunized with monoclonal GLXA-$Ab_2$ developed a significantly high GLXA-$Ab_3$ titer against purified GLXA compared to the control group. The average titer was as high as 1:3200 comparing with 1:200 in the mice immunized with normal mouse IgG. This clearly demonstrates that the production of GLXA-$Ab_3$ antibody in syngeneic mice is elicited by the hypervariable region, the structure which mimics the GLXA. In addition, the GLXA-$Ab_3$ from these mice inhibited the binding of monoclonal GLXA-$Ab_1$ to GLXA as efficiently as unlabeled monoclonal GLXA-$Ab_1$. These experiments show that monoclonal GLXA-$Ab_2$ mimics one single epitope of GLXA.

The protection of mice from ocular infection by *C. trachomatous* was consistently demonstrated in four individual experiments in vivo. The mice immunized with monoclonal GLXA-$Ab_2$ or normal mouse IgG (three times on a weekly basis) were infected in the eyes by inoculation of EBs (5000 IFU/eye). The conjunctival swaps were taken on different days before and after the infection. Inclusions were detected by cell culture. The eyes of the mice immunized with monoclonal GLXA-$Ab_2$ IgG have significantly short recovery (9 days after ocular inoculation comparing to 28 days of the control immunized with normal mouse IgG). The GLXA-$Ab_3$ titer is well correlated with cell culture results. This demonstrates that monoclonal GLXA-$Ab_2$ which mimics a single GLXA epitope is an effective immunogen, evoking a strong protective immune response against chlamydial infection. This shows that a single protective epitope resides on chlamydial GLXA.

Prospective of the mechanism of the neutralization and protection

This example is the first demonstration that a non-neutralizing monoclonal GLXA-$Ab_1$ can produce a neutralizing GLXA-$Ab_3$ in vivo through an anti-idiotypic antibody (GLXA-$Ab_2$). The central issue is that monoclonal GLXA-$Ab_1$ produced by immunization with chlamydial EBs does not neutralize or protect primates from reinfection whereas GLXA $Ab_3$ produced by guinea pig GLXA-$Ab_2$ neutralized the infection and immunization with monoclonal GLXA-$Ab_2$ protects mice from reinfection.

We claim:

1. A monoclonal anti-idiotypic antibody for inducing in an animal an anti-anti-idiotypic antibody which recognizes an antigen comprising a genus specific chlamydial glycolipid exoantigen (GLXA).

2. A continuous hybrid cell line that produces a monoclonal anti-idiotypic antibody which induces in the animal an anti-anti-idiotypic antibody which recognizes an antigen comprising a genus specific chlamydial glycolipid exoantigen (GLXA).

3. The continuous hybrid cell line of claim 2, ATCC Acc. No H.B. 11301.

4. The cell line of claim 2 wherein the cell line is a hybrid of an immune spleen cell which produces an anti-idiotypic antibody which induces in an animal an anti-anti-idiotypic antibody which recognizes an antigen comprising a genus specific chlamydial glycolipid exoantigen (GLXA).

5. A vaccine administered to an animal comprising an amount sufficient to effectively immunize said animal against chlamydia infection in the animal which comprises a biologically active composition selected from the group consisting of a monoclonal anti-idiotypic antibody which induces in the animal an anti-anti-idiotypic antibody which recognizes an antigen comprising a genus-specific chlamydia glycolipid exoantigen (GLXA), a Fab fragment of said anti-idiotypic antibody and mixtures thereof and a pharmaceutically acceptable adjuvant.

6. A vaccine administered to an animal comprising an amount sufficient to effectively immunize said animal against chlamydial infection in the animal which comprises a biologically active composition selected from the group consisting of the monoclonal anti-idiotypic antibody which induces in the animal an anti-anti-idiotypic antibody which recognizes an antigen comprising a genus-specific chlamydia glycolipid exoantigen (GLXA) produced by continuous cell line ATCC Acc. No. H.B.11301, a Fab fragment of said anti-idiotypic antibody and mixtures thereof and a pharmaceutically acceptable adjuvant.

7. The vaccine of claim 5 wherein the adjuvant is aluminum hydroxide.

8. The vaccine of claim 6 wherein the adjuvant is aluminum hydroxide.

9. The vaccine of claim 5 wherein the animal is a human.

10. The vaccine of claim 6 wherein the animal is a human.

11. The vaccine of claim 7 wherein the animal is a human.

12. The vaccine of claim 8 wherein said animal is a human.

13. The process for immunizing an animal against chlamydial infection which comprises administering to said animal a biologically active composition selected from the group consisting of a monoclonal anti-idiotypic antibody which induces in said animal an anti-anti-idiotypic antibody which recognizes a genus specific chlamydia glycolipid exoantigen (GLXA), a Fab fragment of said anti-idiotypic antibody and mixtures thereof in an amount sufficient to effect immunization against chlamydial infection.

14. The process of claim 13 wherein anti-idiotypic antibody is produced by continuous cell line ATCC Acc. No. H.B. 11301.

15. The process of claim 13 wherein said animal is a human.

16. The process of claim 14 wherein said animal is a human.

17. The monoclonal antibody produced by the cell line of claim 3.

* * * * *